(12) United States Patent
Stockley et al.

(10) Patent No.: US 11,059,809 B2
(45) Date of Patent: Jul. 13, 2021

(54) SUBSTITUTED CYANOPYRROLIDINES WITH ACTIVITY AS DUB INHIBITORS

(71) Applicant: MISSION THERAPEUTICS LIMITED, Cambridge (GB)

(72) Inventors: Martin Lee Stockley, Cambridge (GB); Mark Ian Kemp, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/615,709

(22) PCT Filed: Jun. 19, 2018

(86) PCT No.: PCT/GB2018/051691
§ 371 (c)(1),
(2) Date: Nov. 21, 2019

(87) PCT Pub. No.: WO2018/234775
PCT Pub. Date: Dec. 27, 2018

(65) Prior Publication Data
US 2020/0172519 A1 Jun. 4, 2020

(30) Foreign Application Priority Data

Jun. 20, 2017 (GB) ................... 1709824
Mar. 6, 2018 (GB) ................... 1803561

(51) Int. Cl.
*C07D 403/12* (2006.01)
*A61P 25/28* (2006.01)
*A61P 35/00* (2006.01)

(52) U.S. Cl.
CPC ............ *C07D 403/12* (2013.01); *A61P 25/28* (2018.01); *A61P 35/00* (2018.01)

(58) Field of Classification Search
CPC ......... C07D 403/12; A61P 25/28; A61P 35/00
See application file for complete search history.

(56) References Cited

U.S. PATENT DOCUMENTS

2008/0300268 A1   12/2008   Singh et al.

FOREIGN PATENT DOCUMENTS

| WO | 0177073 A1 | 10/2001 | |
|---|---|---|---|
| WO | 03088908 A2 | 10/2003 | |
| WO | 2009026197 A1 | 2/2009 | |
| WO | 2009129365 A1 | 10/2009 | |
| WO | 2009129370 A1 | 10/2009 | |
| WO | 2009129371 A1 | 10/2009 | |
| WO | 2013030218 A1 | 3/2013 | |
| WO | 2015017502 A1 | 2/2015 | |
| WO | 2015179190 A1 | 11/2015 | |
| WO | WO-2015/183987 A1 * | 12/2015 | ............ A61K 38/38 |
| WO | 2016019237 A1 | 2/2016 | |
| WO | 2016046530 A1 | 3/2016 | |
| WO | 2016156816 A1 | 10/2016 | |
| WO | 2017/009650 A1 | 1/2017 | |
| WO | 2017/093718 A1 | 6/2017 | |
| WO | 2017/109488 A1 | 6/2017 | |
| WO | 2017103614 A1 | 6/2017 | |
| WO | 2017/141036 A1 | 8/2017 | |
| WO | 2017/149313 A1 | 9/2017 | |
| WO | 2017/158381 A1 | 9/2017 | |
| WO | 2017/158388 A1 | 9/2017 | |
| WO | 2017/163078 A1 | 9/2017 | |
| WO | 2018060689 A1 | 4/2018 | |
| WO | 2018060691 A1 | 4/2018 | |
| WO | 2018060742 A1 | 4/2018 | |
| WO | 2018065768 A1 | 4/2018 | |
| WO | 2018220355 A1 | 12/2018 | |

OTHER PUBLICATIONS

Chemical Abstracts Registry No. 1821517-32-1, indexed in the Registry file on STN CAS Online Dec. 1, 2015. (Year: 2015).*
Golub et al., Science, vol. 286, Oct. 15, 1999, pp. 531-537. (Year: 1999).*
The International Search Report and Written Opinion, dated Aug. 10, 2018, in the corresponding PCT Appl. No. PCT/GB2018/051691.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.
Clague et al., "Deubiquitylases from genes to organism", Physiol. Rev. 93:1289-1315, 2013.
Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.
Deaton et al, "Novel and potent cyclic cyanamide-based cathepsin K inhibitors", Bioorganic & Medicinal Chemistry Letters 15 (2005) 1815-1819.
Oballa et al, "A generally applicable method for assessing the electrophilicity and reactivity of diverse nitrile-containing compounds", Bioorganic & Medicinal Chemistry Letters 17 (2007) 998-1002.

(Continued)

*Primary Examiner* — Laura L Stockton

(57) ABSTRACT

The present invention relates to a class of substituted-cyanopyrrolidines of formula (Ia), (Ib), and (Ic), with activity as inhibitors of deubiquitilating enzymes, in particular, ubiquitin C-terminal hydrolase 30 or ubiquitin specific peptidase 30 (USP30), having utility in a variety of therapeutic areas including cancer and conditions involving mitochondrial dysfunction (Ia).

(Ia)

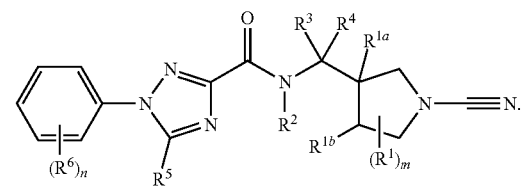

16 Claims, No Drawings

(56) References Cited

OTHER PUBLICATIONS

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.
Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.
Bingol et al, "The mitochondrial deubiquitinase USP30 opposes parkin-mediated mitophagy", Nature vol. 510, 370-375, 2014.
Liang et al, "USP30 deubiquitylates mitochondrial Parkin substrates and restricts apoptotic cell death", EMBO Reports, 1-10, 2015; DOI 10.15252/embr.201439820.
Bedford et al., "Ubiquitin-like protein conjugation and the ubiquitin-proteasome system as drug targets," Nat Rev Drug Discov. Jan. 2011;10(1):29-46.
CAS Registry No. 1521229-30-0; Supplier: AuroraFineChemicals. com Catalogue ID No. A11.642.254, accessed Sep. 18, 2019.
Ward et al., "Quantitative Chemical Proteomic Profiling of Ubiquitin Specific Proteases in Intact Cancer Cells," ACS Chem. Biol. 2016, 11, 3268-3272.

\* cited by examiner

SUBSTITUTED CYANOPYRROLIDINES WITH ACTIVITY AS DUB INHIBITORS

CROSS-REFERENCE TO RELATED APPLICATIONS

This application is a National Stage Application of PCT/GB2018/051691 filed Jun. 19, 2018, which claims priority from UK Patent Application No. 1709824.5, filed on Jun. 20, 2017 and UK Patent Application No. 1803561.8, filed on Mar. 6, 2018. The priority of said PCT and UK Patent Applications are claimed.

The present invention relates to a class of substituted-cyanopyrrolidines with activity as inhibitors of deubiquitilating enzymes, in particular, ubiquitin C-terminal hydrolase 30 or ubiquitin specific peptidase 30 (USP30), uses thereof, processes for the preparation thereof and composition containing said inhibitors. These inhibitors have utility in a variety of therapeutic areas including cancer and conditions involving mitochondrial dysfunction.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011).

Accordingly, there is a need for compounds that are inhibitors of USP30 for the treatment of indications where inhibition of USP30 is indicated.

Series of derivatives of cyano-substituted heterocycles are disclosed as deubiquitylating enzyme inhibitors in PCT applications WO 2016/046530, WO 2016/156816, WO 2017/009650, WO 2017/093718, WO 2017/103614, WO 2017/149313, WO 2017/109488, WO 2017/141036, WO 2017/163078, WO 2017/158381, WO 2017/158388, PCT/GB2017/052971, PCT/GB2017/052949, PCT/GB2017/052880, and PCT/GB2017/052882. Falgueyret et al., J. Med. Chem. 2001, 44, 94-104, and PCT application WO 01/77073 refer to cyanopyrrolidines as inhibitors of Cathepsins K and L, with potential utility in treating osteoporosis and other bone-resorption related conditions. PCT application WO 2015/179190 refers to N-acylethanolamine hydrolysing acid amidase inhibitors, with potential utility in treating ulcerative colitis and Crohn's disease. PCT application WO 2013/030218 refers to quinazolin-4-one compounds as inhibitors of ubiquitin specific proteases, such as USP7, with potential utility in treating cancer, neurodegenerative diseases, inflammatory disorders and viral infections. PCT applications WO 2015/017502 and WO 2016/019237 refer to inhibitors of Bruton's tyrosine kinase with potential utility in treating disease such as autoimmune disease, inflammatory disease and cancer. PCT applications WO 2009/026197, WO 2009/129365, WO 2009/129370, and WO 2009/129371, refer to cyanopyrrolidines as inhibitors of Cathepsin C with potential utility in treating COPD. United States patent application US 2008/0300268 refers to polyaromatic compounds as inhibitors of tyrosine kinase receptor PDGFR.

According to a first aspect, the present invention provides a compound of formula (I), which is selected from (Ia), (Ib), and (Ic):

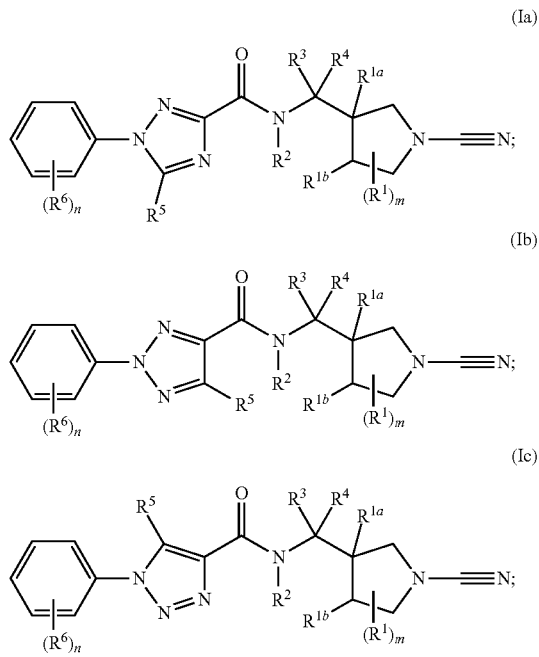

a tautomer thereof, or a pharmaceutically acceptable salt of said compound or tautomer, wherein:

m is 0 to 5;
n is 0 to 5;
each $R^1$ is independently selected from halo, cyano, hydroxy, $(C_1-C_6)$alkyl, $(C_1-C_6)$alkoxy, halo$(C_1-C_6)$alkyl, halo$(C_1-C_6)$alkoxy, and $(C_1-C_6)$alkoxy$(C_1-C_6)$alkyl;

$R^{1a}$ and $R^{1b}$, are each independently selected from hydrogen, halo, cyano, hydroxy, $(C_1-C_6)$alkyl, $(C_1-C_6)$alkoxy, halo$(C_1-C_6)$alkyl, halo$(C_1-C_6)$alkoxy, and $(C_1-C_6)$alkoxy$(C_1-C_6)$alkyl;

$R^2$ is selected from hydrogen, $(C_1-C_6)$alkyl, and $(C_1-C_6)$alkoxy$(C_1-C_6)$alkyl;

or $R^{1b}$ together with $R^2$ may form a 5 to 6-membered heterocyclic ring containing 1 to 2 heteroatoms independently selected from N, O and S, at least one of which is N; wherein said heterocyclic ring may be optionally further substituted with 1 to 4 substituents independently selected from halo, cyano, hydroxy, oxo, $(C_1-C_6)$alkyl, $(C_1-C_6)$alkoxy, $(C_1-C_6)$alkoxy$(C_1-C_6)$alkyl, halo$(C_1-C_6)$alkyl, and halo$(C_1-C_6)$alkoxy;

$R^3$ and $R^4$ are each independently selected from hydrogen, cyano, and $(C_1-C_6)$alkyl; or $R^3$ and $R^4$ together form a 3 to 6 membered cycloalkyl ring;

$R^5$ is selected from hydrogen, halo, cyano, hydroxy, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy, NH$(C_1-C_6)$alkyl, N$((C_1-C_6)$alkyl$)_2$, C(O)NH$(C_1-C_6)$alkyl, C(O)N$((C_1-C_6)$alkyl$)_2$, NHC(O)$(C_1-C_6)$alkyl, N$((C_1-C_6)$alkyl)C(O)$(C_1-C_6)$alkyl), C(O)$(C_1-C_6)$alkyl, C(O)O$(C_1-C_6)$alkyl, $CO_2H$, $CONH_2$, $SO_2NH(C_1-C_6)$alkyl, and $SO_2N((C_1-C_6)$alkyl$)_2$; and each $R^6$ is independently selected from halo, cyano, hydroxy, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy, NH$(C_1-C_6)$alkyl, N$((C_1-C_6)$alkyl$)_2$, C(O)NH$(C_1-C_6)$alkyl, C(O)N$((C_1-C_6)$alkyl$)_2$, NHC(O)$(C_1-C_6)$alkyl, N$((C_1-C_6)$alkyl)C(O)$(C_1-C_6)$alkyl), C(O)$(C_1-C_6)$alkyl, C(O)O$(C_1-C_6)$alkyl, $CO_2H$, $CONH_2$, $SO_2NH(C_1-C_6)$alkyl, and $SO_2N((C_1-C_6)$alkyl$)_2$.

Unless otherwise indicated, alkyl, and alkoxy groups, including the corresponding divalent radicals, may be straight or branched and contain 1 to 6 carbon atoms and typically 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy. Cycloalkyl includes, for example. cyclopropyl.

Halo means fluoro, chloro, bromo or iodo, in particular, fluoro or chloro. Haloalkyl and haloalkoxy groups may contain one or more halo substituents. Examples are trifluoromethyl and trifluoromethoxy. Heterocyclic rings may be saturated, or partially unsaturated.

Unless otherwise indicated, the term substituted means substituted by one or more defined groups. In the case where groups may be selected from more than one alternatives, the selected groups may be the same or different. The term independently means that where more than one substituent is selected from more than one possible substituents, those substituents may be the same or different.

Preferred embodiments of the compound of formula (I) for use in the present invention are defined below.

Preferably, m is selected from 0, 1, 2, 3 and 4.
More preferably, m is 0, 1 or 2.
Yet more preferably, m is 0 or 1.
Most preferably, m is 0.
Preferably, n is selected from 0, 1, 2, 3, and 4.
More preferably, n is 0, 1 or 2.
Most preferably, n is 1 or 2.
Preferably, each $R^1$ is independently selected from halo, cyano, hydroxy, $(C_1-C_3)$alkyl, $(C_1-C_3)$alkoxy, halo$(C_1-C_3)$alkyl, halo$(C_1-C_3)$alkoxy, and $(C_1-C_3)$alkoxy$(C_1-C_3)$alkyl.
More preferably, each $R^1$ is independently selected from chloro, fluoro, methyl, ethyl, and methoxy.
Most preferably, $R^1$ is methyl.
Preferably, $R^{1a}$ is selected from hydrogen, halo, cyano, hydroxy, $(C_1-C_3)$alkyl, $(C_1-C_3)$alkoxy, halo$(C_1-C_3)$alkyl, halo$(C_1-C_3)$alkoxy, and $(C_1-C_3)$alkoxy$(C_1-C_3)$alkyl. More preferably, $R^{1a}$ is selected from hydrogen, chloro, fluoro, cyano, hydroxy, methyl, ethyl, methoxy, and methoxymethyl.
Yet more preferably, $R^{1a}$ is selected from hydrogen and fluoro.
Most preferably, $R^{1a}$ is hydrogen.
In one preferred embodiment, wherein $R^{1b}$ and $R^2$ are independent:
Preferably, $R^{1b}$ is selected from hydrogen, halo, cyano, hydroxy, $(C_1-C_3)$alkyl, $(C_1-C_3)$alkoxy, halo$(C_1-C_3)$alkyl, halo$(C_1-C_3)$alkoxy, and $(C_1-C_3)$alkoxy$(C_1-C_3)$alkyl.
More preferably, $R^{1b}$ is selected from hydrogen, chloro, fluoro, cyano, hydroxy, methyl, ethyl, methoxy, and methoxymethyl.
Yet more preferably, $R^{1b}$ is selected from hydrogen, and methyl.
Most preferably, $R^{1b}$ is hydrogen.
Preferably, $R^2$ is selected from hydrogen, $(C_1-C_3)$alkyl, and $(C_1-C_3)$alkoxy$(C_1-C_3)$alkyl.
More preferably, $R^2$ is selected from hydrogen, methyl, ethyl, propyl, and methoxyethyl.

Yet more preferably, $R^2$ is selected from hydrogen, methyl, and ethyl.

Most preferably, $R^2$ is selected from hydrogen and methyl.

In another preferred embodiment, $R^{1b}$ together with $R^2$ forms a 5 to 6-membered heterocyclic ring containing 1 to 2 heteroatoms independently selected from N, O and S, at least one of which is N;

wherein said heterocyclic ring may be optionally further substituted with 1 to 4, and preferably 1 to 2, substituents independently selected from fluoro, chloro, cyano, hydroxy, oxo, methyl, and methoxy.

More preferably, $R^{1b}$ together with $R^2$ forms a 5 to 6-membered heterocyclic ring containing 1 nitrogen atom;

wherein said heterocyclic ring may be optionally further substituted with 1 to 2 substituents independently selected from fluoro, chloro, cyano, hydroxy, oxo, methyl, and methoxy. Most preferably, said heterocyclic ring may be optionally further substituted with 1 to 2 substituents independently selected from fluoro, oxo, and methyl.

Preferably, $R^3$ and $R^4$ are each independently selected from hydrogen, cyano, methyl, ethyl, and propyl; or $R^3$ and $R^4$ together form a cyclopropyl ring.

More preferably, $R^3$ is selected from hydrogen and methyl.

Most preferably, $R^3$ is hydrogen.

More preferably, $R^4$ is selected from hydrogen, cyano and methyl.

Most preferably, $R^4$ is hydrogen.

Preferably, $R^5$ is selected from hydrogen, halo, cyano, hydroxy, $(C_1-C_3)$alkyl, $(C_1-C_3)$alkoxy, $(C_1-C_3)$alkoxy$(C_1-C_3)$alkyl, halo$(C_1-C_3)$alkyl, halo$(C_1-C_3)$alkoxy, $NH(C_1-C_3)$alkyl, $N((C_1-C_3)$alkyl$)_2$, $C(O)NH(C_1-C_3)$alkyl, $C(O)N((C_1-C_3)$alkyl$)_2$, $NHC(O)(C_1-C_3)$alkyl, $N((C_1-C_3)$alkyl$)C(O)(C_1-C_3)$alkyl), $C(O)(C_1-C_3)$alkyl, $C(O)O(C_1-C_3)$alkyl, $CO_2H$, $CONH_2$, $SO_2NH(C_1-C_3)$alkyl, and $SO_2N((C_1-C_3)$alkyl$)_2$. More preferably, $R^5$ is selected from hydrogen, chloro, fluoro, cyano, hydroxy, $(C_1-C_3)$alkyl, $(C_1-C_3)$alkoxy, $(C_1-C_3)$alkoxy$(C_1-C_3)$alkyl, halo$(C_1-C_3)$alkyl, and halo$(C_1-C_3)$alkoxy.

Yet more preferably, $R^5$ is selected from hydrogen, chloro, fluoro, cyano, hydroxy, methyl, ethyl, propyl, methoxy, ethoxy, and methoxymethyl.

Most preferably, $R^5$ is selected from hydrogen and methyl.

Preferably, each $R^6$ is independently selected from halo, cyano, hydroxy, $(C_1-C_3)$alkyl, $(C_1-C_3)$alkoxy, $(C_1-C_3)$alkoxy$(C_1-C_3)$alkyl, halo$(C_1-C_3)$alkyl, halo$(C_1-C_3)$alkoxy, $NH(C_1-C_3)$alkyl, $N((C_1-C_3)$alkyl$)_2$, $C(O)NH(C_1-C_3)$alkyl, $C(O)N((C_1-C_3)$alkyl$)_2$, $NHC(O)(C_1-C_3)$alkyl, $N((C_1-C_3)$alkyl$)C(O)(C_1-C_3)$alkyl), $C(O)(C_1-C_3)$alkyl, $C(O)O(C_1-C_3)$alkyl, $CO_2H$, $CONH_2$, $SO_2NH(C_1-C_3)$alkyl, and $SO_2N((C_1-C_3)$alkyl$)_2$.

More preferably, each $R^6$ is independently selected from chloro, fluoro, cyano, hydroxy, $(C_1-C_3)$alkyl, $(C_1-C_3)$alkoxy, $(C_1-C_3)$alkoxy$(C_1-C_3)$alkyl, halo$(C_1-C_3)$alkyl, and halo$(C_1-C_3)$alkoxy.

Yet more preferably, each $R^6$ is independently selected from chloro, fluoro, cyano, hydroxy, methyl, ethyl, propyl, methoxy, ethoxy, methoxymethyl, $CF_3$, and $OCF_3$. Most preferably, each $R^6$ is independently selected from chloro and cyano.

According to one particularly preferred embodiment of the first aspect of the invention, the compound of formula (I) is a compound of formula (Ia):

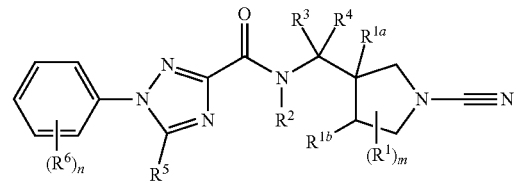

(Ia)

wherein m, n, $R^1$, $R^{1a}$, $R^{1b}$, $R^2$, $R^3$, $R^4$, $R^5$, and $R^6$, are as defined in respect of the first aspect of the invention and preferred embodiments thereof; a tautomer thereof, or a pharmaceutically acceptable salt of said compound or tautomer.

According to one example of a preferred embodiment of the first aspect of the invention, the compound of formula (I) is a compound of formula (Ia) wherein:

m is 0, 1 or 2;

n is 0, 1 or 2;

each $R^1$ is independently selected from halo, cyano, hydroxy, $(C_1-C_3)$alkyl, $(C_1-C_3)$alkoxy, halo$(C_1-C_3)$alkyl, halo$(C_1-C_3)$alkoxy, and $(C_1-C_3)$alkoxy$(C_1-C_3)$alkyl;

$R^{1a}$ is selected from hydrogen, halo, cyano, hydroxy, $(C_1-C_3)$alkyl, $(C_1-C_3)$alkoxy, halo$(C_1-C_3)$alkyl, halo$(C_1-C_3)$alkoxy, and $(C_1-C_3)$alkoxy$(C_1-C_3)$alkyl;

$R^{1b}$ is selected from hydrogen, halo, cyano, hydroxy, $(C_1-C_3)$alkyl, $(C_1-C_3)$alkoxy, halo$(C_1-C_3)$alkyl, halo$(C_1-C_3)$alkoxy, and $(C_1-C_3)$alkoxy$(C_1-C_3)$alkyl;

$R^2$ is selected from hydrogen, $(C_1-C_3)$alkyl, and $(C_1-C_3)$alkoxy$(C_1-C_3)$alkyl;

or $R^{1b}$ together with $R^2$ may form a 5 to 6-membered heterocyclic ring containing 1 to 2 heteroatoms independently selected from N, O and S, at least one of which is N;

said heterocyclic ring may be optionally further substituted with 1 to 4, and preferably 1 to 2, substituents independently selected from fluoro, chloro, cyano, hydroxy, oxo, methyl, and methoxy;

$R^3$ and $R^4$ are each independently selected from hydrogen, cyano, methyl, ethyl, and propyl; or $R^3$ and $R^4$ together form a cyclopropyl ring;

$R^5$ is selected from hydrogen, chloro, fluoro, cyano, hydroxy, $(C_1-C_3)$alkyl, $(C_1-C_3)$alkoxy, $(C_1-C_3)$alkoxy$(C_1-C_3)$alkyl, halo$(C_1-C_3)$alkyl, and halo$(C_1-C_3)$alkoxy; and each $R^6$ is independently selected from chloro, fluoro, cyano, hydroxy, $(C_1-C_3)$alkyl, $(C_1-C_3)$alkoxy, $(C_1-C_3)$alkoxy$(C_1-C_3)$alkyl, halo$(C_1-C_3)$alkyl, and halo$(C_1-C_3)$alkoxy;

a tautomer thereof, or a pharmaceutically acceptable salt of said compound or tautomer.

According to another example of a more preferred embodiment of the first aspect of the invention, the compound of formula (I) is a compound of formula (Ia) wherein:

m is 0 or 1;

n is 1 or 2;

$R^1$ is selected from chloro, fluoro, methyl, ethyl, and methoxy;

$R^{1a}$ is selected from hydrogen, chloro, fluoro, cyano, hydroxy, methyl, ethyl, methoxy, and methoxymethyl;

$R^{1b}$ is selected from hydrogen, chloro, fluoro, cyano, hydroxy, methyl, ethyl, methoxy, and methoxymethyl;

$R^2$ is selected from hydrogen, methyl, ethyl, propyl, and methoxyethyl;

or $R^{1b}$ together with $R^2$ forms a 5 to 6-membered heterocyclic ring containing 1 nitrogen atom;

said heterocyclic ring may be optionally further substituted with 1 to 2 substituents independently selected from fluoro, chloro, cyano, hydroxy, oxo, methyl, and methoxy;

$R^3$ and $R^4$ are each independently selected from hydrogen, cyano, methyl, ethyl, and propyl; or $R^3$ and $R^4$ together form a cyclopropyl ring;

$R^5$ is selected from hydrogen, chloro, fluoro, cyano, hydroxy, methyl, ethyl, propyl, methoxy, ethoxy, and methoxymethyl; and each $R^6$ is independently selected from chloro, fluoro, cyano, hydroxy, methyl, ethyl, propyl, methoxy, ethoxy, methoxymethyl, $CF_3$, and $OCF_3$;

a tautomer thereof, or a pharmaceutically acceptable salt of said compound or tautomer.

According to another example of a yet more preferred embodiment of the first aspect of the invention, the compound of formula (I) is a compound of formula (Ia) wherein:

m is 0 or 1;
n is 1 or 2;
$R^1$ is methyl;
$R^{1a}$ is selected from hydrogen and fluoro;
$R^{1b}$ is selected from hydrogen and methyl;
$R^2$ is selected from hydrogen and methyl;
$R^3$ is selected from hydrogen and methyl;
$R^4$ is selected from hydrogen, cyano and methyl;
$R^5$ is selected from hydrogen and methyl; and
each $R^6$ is independently selected from chloro and cyano;
a tautomer thereof, or a pharmaceutically acceptable salt of said compound or tautomer.

According to another particularly preferred embodiment of the first aspect of the invention, the compound of formula (I) is a compound of formula (Ib):

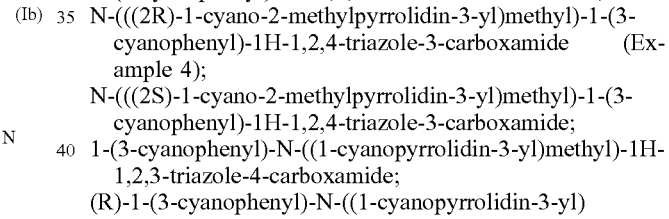

(Ib)

wherein m, n, $R^1$, $R^{1a}$, $R^{1b}$, $R^2$, $R^3$, $R^4$, $R^5$, and $R^6$, are as defined in respect of the first aspect of the invention and preferred embodiments thereof; a tautomer thereof, or a pharmaceutically acceptable salt of said compound or tautomer.

Examples of preferred embodiments of the compound of formula (Ib) correspond to the above-mentioned examples of the preferred embodiments of the compound of formula (Ia).

According to another particularly preferred embodiment of the first aspect of the invention, the compound of formula (I) is a compound of formula (Ic):

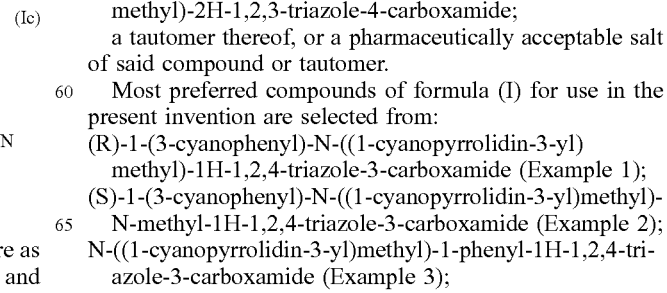

(Ic)

wherein m, n, $R^1$, $R^{1a}$, $R^{1b}$, $R^2$, $R^3$, $R^4$, $R^5$, and $R^6$, are as defined in respect of the first aspect of the invention and preferred embodiments thereof; a tautomer thereof, or a pharmaceutically acceptable salt of said compound or tautomer.

Examples of preferred embodiments of the compound of formula (Ic) correspond to the above-mentioned examples of the preferred embodiments of the compound of formula (Ia).

Preferred compounds of formula (I) for use in the present invention are selected from:

1-(3-cyanophenyl)-N-((1-cyanopyrrolidin-3-yl)methyl)-1H-1,2,4-triazole-3-carboxamide;
(R)-1-(3-cyanophenyl)-N-((1-cyanopyrrolidin-3-yl)methyl)-1H-1,2,4-triazole-3-carboxamide;
(S)-1-(3-cyanophenyl)-N-((1-cyanopyrrolidin-3-yl)methyl)-1H-1,2,4-triazole-3-carboxamide;
1-(3-cyanophenyl)-N-((1-cyanopyrrolidin-3-yl)methyl)-N-methyl-1H-1,2,4-triazole-3-carboxamide;
(R)-1-(3-cyanophenyl)-N-((1-cyanopyrrolidin-3-yl)methyl)-N-methyl-1H-1,2,4-triazole-3-carboxamide;
(S)-1-(3-cyanophenyl)-N-((1-cyanopyrrolidin-3-yl)methyl)-N-methyl-1H-1,2,4-triazole-3-carboxamide;
N-((1-cyanopyrrolidin-3-yl)methyl)-1-phenyl-1H-1,2,4-triazole-3-carboxamide;
(R)—N-((1-cyanopyrrolidin-3-yl)methyl)-1-phenyl-1H-1,2,4-triazole-3-carboxamide;
(S)—N-((1-cyanopyrrolidin-3-yl)methyl)-1-phenyl-1H-1,2,4-triazole-3-carboxamide;
N-(((2R,3R)-1-cyano-2-methylpyrrolidin-3-yl)methyl)-1-(3-cyanophenyl)-1H-1,2,4-triazole-3-carboxamide;
N-(((2R,3S)-1-cyano-2-methylpyrrolidin-3-yl)methyl)-1-(3-cyanophenyl)-1H-1,2,4-triazole-3-carboxamide;
N-(((2S,3S)-1-cyano-2-methylpyrrolidin-3-yl)methyl)-1-(3-cyanophenyl)-1H-1,2,4-triazole-3-carboxamide;
N-(((2S,3R)-1-cyano-2-methylpyrrolidin-3-yl)methyl)-1-(3-cyanophenyl)-1H-1,2,4-triazole-3-carboxamide;
N-(((2R)-1-cyano-2-methylpyrrolidin-3-yl)methyl)-1-(3-cyanophenyl)-1H-1,2,4-triazole-3-carboxamide (Example 4);
N-(((2S)-1-cyano-2-methylpyrrolidin-3-yl)methyl)-1-(3-cyanophenyl)-1H-1,2,4-triazole-3-carboxamide;
1-(3-cyanophenyl)-N-((1-cyanopyrrolidin-3-yl)methyl)-1H-1,2,3-triazole-4-carboxamide;
(R)-1-(3-cyanophenyl)-N-((1-cyanopyrrolidin-3-yl)methyl)-1H-1,2,3-triazole-4-carboxamide;
(S)-1-(3-cyanophenyl)-N-((1-cyanopyrrolidin-3-yl)methyl)-1H-1,2,3-triazole-4-carboxamide;
1-(3-chlorophenyl)-N-((1-cyanopyrrolidin-3-yl)methyl)-1H-1,2,3-triazole-4-carboxamide;
(R)-1-(3-chlorophenyl)-N-((1-cyanopyrrolidin-3-yl)methyl)-1H-1,2,3-triazole-4-carboxamide;
(S)-1-(3-chlorophenyl)-N-((1-cyanopyrrolidin-3-yl)methyl)-1H-1,2,3-triazole-4-carboxamide;
2-(3-chlorophenyl)-N-((1-cyanopyrrolidin-3-Amethyl)-2H-1,2,3-triazole-4-carboxamide;
(R)-2-(3-chlorophenyl)-N-((1-cyanopyrrolidin-3-yl)methyl)-2H-1,2,3-triazole-4-carboxamide; and
(S)-2-(3-chlorophenyl)-N-((1-cyanopyrrolidin-3-yl)methyl)-2H-1,2,3-triazole-4-carboxamide;
a tautomer thereof, or a pharmaceutically acceptable salt of said compound or tautomer.

Most preferred compounds of formula (I) for use in the present invention are selected from:
(R)-1-(3-cyanophenyl)-N-((1-cyanopyrrolidin-3-yl)methyl)-1H-1,2,4-triazole-3-carboxamide (Example 1);
(S)-1-(3-cyanophenyl)-N-((1-cyanopyrrolidin-3-yl)methyl)-N-methyl-1H-1,2,4-triazole-3-carboxamide (Example 2);
N-((1-cyanopyrrolidin-3-yl)methyl)-1-phenyl-1H-1,2,4-triazole-3-carboxamide (Example 3);

N-(((2R)-1-cyano-2-methylpyrrolidin-3-yl)methyl)-1-(3-cyanophenyl)-1H-1,2,4-triazole-3-carboxamide (Example 4);
N-(((2R,3R)-1-cyano-2-methylpyrrolidin-3-yl)methyl)-1-(3-cyanophenyl)-1H-1,2,4-triazole-3-carboxamide (diastereoisomer of Example 4);
N-(((2R,3S)-1-cyano-2-methylpyrrolidin-3-yl)methyl)-1-(3-cyanophenyl)-1H-1,2,4-triazole-3-carboxamide (diastereoisomer of Example 4);
(R)-1-(3-cyanophenyl)-N-((1-cyanopyrrolidin-3-yl)methyl)-1H-1,2,3-triazole-4-carboxamide (Example 5);
(R)-1-(3-chlorophenyl)-N-((1-cyanopyrrolidin-3-yl)methyl)-1H-1,2,3-triazole-4-carboxamide (Example 6);
(R)-2-(3-chlorophenyl)-N-((1-cyanopyrrolidin-3-yl)methyl)-2H-1,2,3-triazole-4-carboxamide (Example 7); and
(R)—N-((1-cyanopyrrolidin-3-yl)methyl)-1-phenyl-1H-1,2,4-triazole-3-carboxamide (Example 8);
a tautomer thereof, or a pharmaceutically acceptable salt of said compound or tautomer.

Pharmaceutical acceptable salts of the compounds of formula (I) include the acid addition and base salts (including di-salts) thereof.

Suitable acid addition salts are formed from acids which form non-toxic salts. Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutical acceptable solvates in accordance with the invention include hydrates and solvates wherein the solvent of crystallization may be isotopically substituted, e.g. $D_2O$, acetone-$d_6$, DMSO-$d_6$.

Also within the scope of the invention are clathrates, drug-host inclusion complexes wherein, in contrast to the aforementioned solvates, the drug and host are present in non-stoichiometric amounts. For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula, including compounds exhibiting more than one type of isomerism, and mixtures of one or more thereof. Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

In particular, the compounds of formula (I) contain a chiral centre at the carbon atom of the pyrrolidine ring that is substituted by $R^{1a}$, and said stereocentre can thus exist in either the (R) or (S) configuration. The designation of the absolute configuration (R) and (S) for stereoisomers in accordance with IUPAC nomenclature is dependent on the nature of the substituents and application of the sequence-rule procedure. The compounds of formula (I) may thus exist in either of the following enantiomeric configurations:

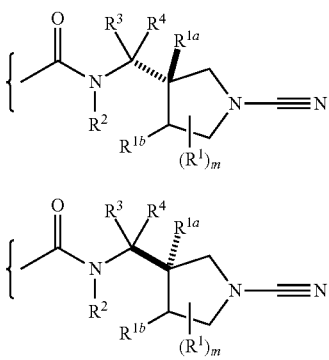

(I)(i)

(I)(ii)

In a preferred aspect, the compounds of formula (I) possess the absolute stereochemical configuration:

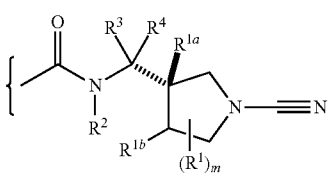

(I)(i)

In another preferred aspect the compounds of formula (I) possess the absolute stereochemical configuration:

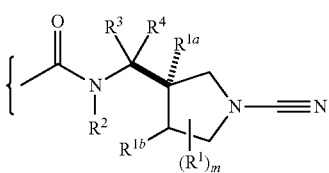

(I)(ii)

Included within the scope of the present invention are each of these (R) and (S) stereoisomers of the compounds of formula (I) in individual form; formula (I)(i), Formula (I)(ii), or mixtures thereof. When the compound of formula (I) is isolated as a single stereoisomer, the compound may exist with an enantiomeric excess of at least 80%, preferably at least 90%, more preferably at least 95%, for example 96%, 97%, 98%, 99%, or 100%.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^{2}H$ and $^{3}H$, carbon, such as $^{13}C$ and $^{14}C$, nitrogen, such as $^{15}N$, oxygen, such as $^{17}O$ and $^{18}O$, phosphorus, such as $^{32}P$, sulphur, such as $^{35}S$, fluorine, such as $^{18}F$, and chlorine, such as $^{38}Cl$.

Substitution of the compounds of the invention with isotopes such as deuterium may afford certain therapeutic advantages resulting from greater metabolic stability, for example, increased in vivo half-life or reduced dosage requirements, and hence may be preferred in some circumstances.

Certain isotopic variations of the compounds of formula (I), for example, those incorporating a radioactive isotope, are useful in drug and/or substrate tissue distribution studies. The radioactive isotopes tritium, and $^{14}C$, are particularly useful for this purpose in view of their ease of incorporation and ready means of detection.

Isotopic variations of the compounds of formula (I) can generally be prepared by conventional techniques known to those skilled in the art or by processes analogous to those described in the accompanying Examples and Preparations using appropriate isotopic variations of suitable reagents.

The compounds of formula (I) are inhibitors of the deubiquitylating enzyme USP30.

According to a further aspect, the present invention provides a compound of formula (I) as defined herein, a tautomer thereof, or a pharmaceutically acceptable salt of said compound or tautomer for use as a medicament.

According to a further aspect, the present invention provides a method of treatment of a disorder or condition where inhibition of USP30 is known, or can be shown, to produce a beneficial effect, in a mammal, comprising administering to said mammal a therapeutically effective amount of a compound of formula (I) as defined herein, a tautomer thereof, or a pharmaceutically acceptable salt of said compound or tautomer.

According to a further aspect, the present invention provides the use of a compound of formula (I) as defined herein, a tautomer thereof, or a pharmaceutically acceptable salt of said compound or tautomer, in the preparation of a medicament for the treatment of a disorder or condition where inhibition of USP30 is known, or can be shown, to produce a beneficial effect.

The disorder or condition benefiting from USP30 activity is selected from a condition involving mitochondrial dysfunction, and cancer.

In one preferred embodiment of all aspects of the invention, the disorder or condition benefiting from USP30 activity is a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS); mitochondrial myopathy; encephalopathy; lactic acidosis; stroke-like episodes (MELAS) syndrome; Leber's hereditary optic neuropathy (LHON); cancer (including, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma); neuropathy, ataxia, retinitis pigmentosa, maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastrointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VL-CAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In particular, the compounds of the invention may be useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyl-transferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

In another preferred embodiment of all aspects of the invention, the disorder or condition benefiting from USP30 activity is cancer. The cancer may be linked to mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

In particular, the compounds of the invention may be useful in the treatment of cancer where apoptotic pathways are dysregulated and more particularly where proteins of the BCL-2 family are mutated, or over or under expressed.

References to 'treatment' includes curative, palliative and prophylactic, and includes means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and other mammals.

According to a further aspect, the present invention provides a pharmaceutical composition comprising a compound of formula (I) as defined herein, or a pharmaceutically acceptable salt of said compound or tautomer, together with a pharmaceutically acceptable diluent or carrier.

Pharmaceutical compositions of the invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention or pharmaceutical compositions thereof, as described herein, may be used alone or combined with one or more additional pharmaceutical agents. The compounds may be combined with an additional anti-tumour therapeutic agent, for example, chemotherapeutic drugs or inhibitors of other regulatory proteins. In one embodiment, the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment, the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any suitably effective manner, such as oral, parenteral, topical, inhaled, intranasal, rectal, intravaginal, ocular, and andial. Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolat and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25 (2), 1-14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Pharmaceutical compositions of the present invention also include compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla.

Dosage

The magnitude of an effective dose of a compound will, of course, vary with the nature of the severity of the condition to be treated and the route of administration. The selection of appropriate dosages is within the remit of the physician. The daily dose range is about 10 µg to about 100 mg per kg body weight of a hum an and non-human animal and in general may be around 10 µg to 30 mg per kg body weight per dose. The above dose may be given from one to three times per day.

For example, oral administration may require a total daily dose of from 5 mg to 1000 mg, such as from 5 to 500 mg, while an intravenous dose may only require from 0.01 to 30 mg/kg body weight, such as from 0.1 to 10 mg/kg, more preferably from 0.1 to 1 mg/kg body weight. The total daily dose may be administered in single or divided doses.

The skilled person will also appreciate that, in the treatment of certain conditions, compounds of the invention may be taken as a single dose on an "as required" basis (i.e. as needed or desired).

Synthetic Methodologies

Compounds of formula (I) may be prepared using methods as described below in the general reaction schemes and the representative examples. Where appropriate, the individual transformations within a scheme may be completed in a different order.

According to a further aspect, the present invention provides a process for the preparation of a compound of formula (I), as defined herein [(Ia), (Ib), (Ic)], comprising reacting a compound of formula (IVa), (IVb), or (IVc), as appropriate, where X is OH with an amine of formula (V), where PG is a protecting group, such as BOC or CBZ, to give an amide of formula (IIIa), (IIIb), or (IIIc) (Scheme 1). The amide-coupling reaction can be performed using standard methodology, for example by reaction using a coupling reagent such as DCC, HATU, HBTU, EDC or via a mixed anhydride. Alternatively, the acids (IVa), (IVb), or (IVc), where X is OH, can be converted into the acid chlorides (IVa), (IVb), or (IVc), where X is Cl, using $SOCl_2$, $PCl_3$, or $PCl_5$, which can then be reacted with the amine (V), preferably in a suitable solvent in the presence of a suitable base. Alternatively, the compound (IVa), (IVb), or (IVc), where X forms the ester, can be reacted directly with the amine (V), preferably in a suitable solvent.

Additionally, one compound of formula (IIIa), (IIIb), or (IIIc) may be converted into another compound of formula (IIIa), (IIIb), or (IIIc), for example via a Suzuki coupling of a bromo-aryl or bromo-heteroaryl group. The compound of formula (IIIa), (IIIb), or (IIIc), may be deprotected using standard methods to give amine (IIa), (IIb), or (IIc), which may then be reacted with cyanogen bromide to give the corresponding compound of formula (I). Scheme 1 illustrates one method that may be used, as applied to the compound of formula (Ia) using the compound of formula (IVa), which applies equally to the preparation of the compounds of formula (Ib) and formula (Ic) using the appropriate corresponding compounds of formula (IVb) and (IVc).

Scheme 1

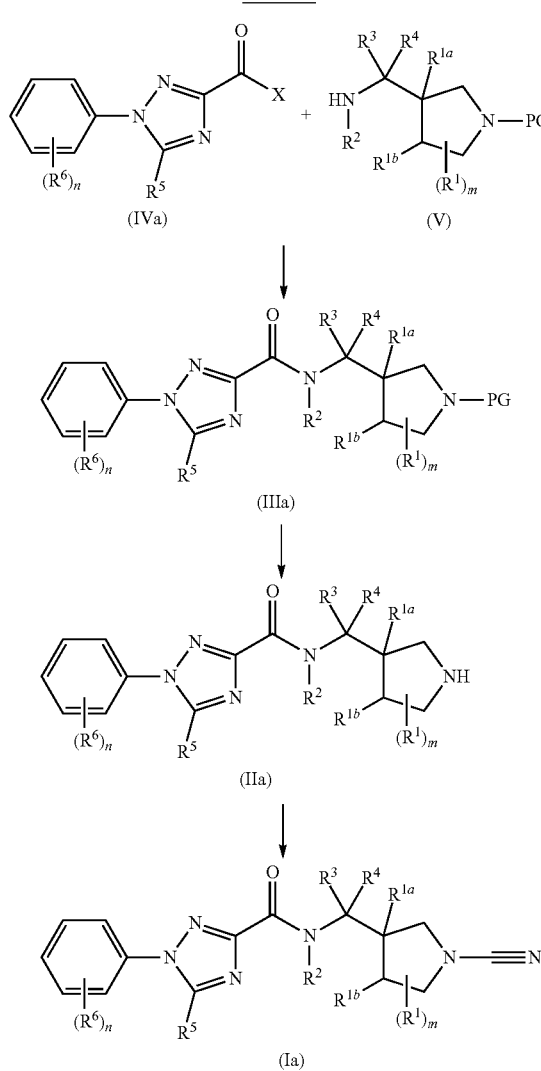

In a further aspect, the present invention provides a compound, which is selected from formulae (IIa), (IIIa), (IIb), (IIIb), (IIc), and (IIIc):

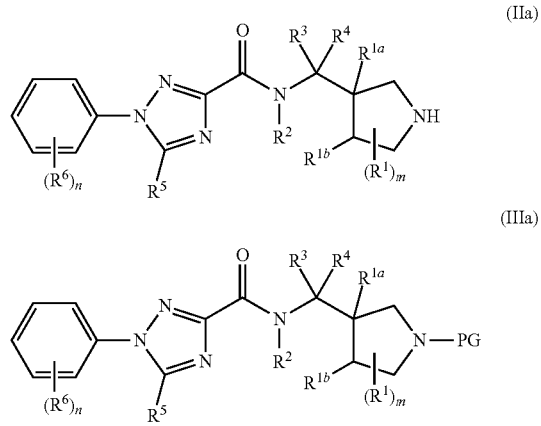

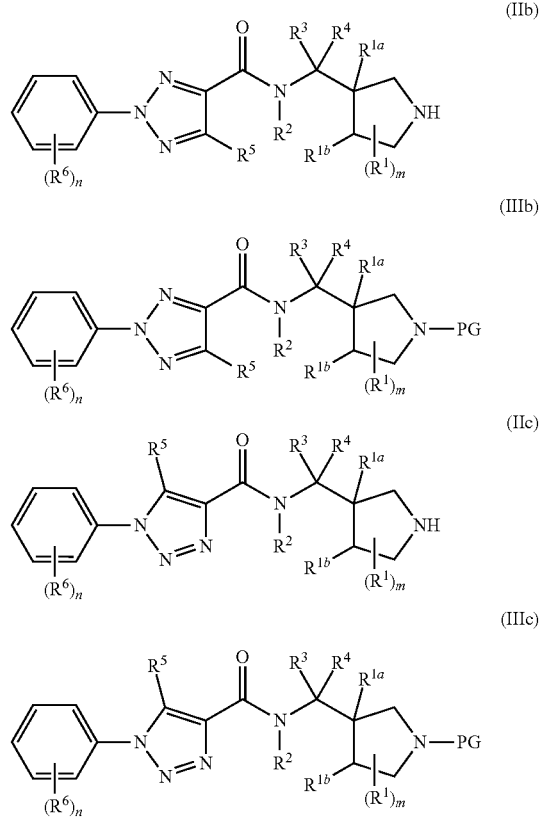

wherein PG is a protecting group, preferably BOC or CBZ, and m, n, $R^1$, $R^{1a}$, $R^{1b}$, $R^2$, $R^3$, $R^4$, $R^5$, and $R^6$, are as defined in any one of claims 1 to 16, a tautomer thereof, or a salt of said compound or tautomer.

In further preferred aspects, the present invention provides a compound, which is selected from formulae (IIa), (IIIa), (IIb), (IIIb), (IIc), and (IIIc), as described herein, in the absolute stereochemical configuration corresponding to the compounds of formula (I), and preferred embodiments thereof.

Additional representative compounds and stereoisomers, racemic mixtures, diastereomers and enantiomers thereof may be prepared using the intermediates prepared in accordance to the general schemes and other materials, compounds and reagents known to those skilled in the art. Enantiomers may be separated using standard techniques, such as Chiral HPLC, for example, using column CHIRAL-ART SA 250×4.6 mm 5 μm.

The invention is illustrated by the following non-limiting examples in which the following abbreviations and definitions are used.

Abbreviations

ACN Acetonitrile
d Doublet (NMR signal)
DBU 1,8-Diazabicyclo[5.4.0]undec-7-ene
DCM Dichloromethane
DIPEA N,N-Diisopropylamine
DMF N,N-Dimethylformamide
DMS Dimethyl sulphide
DMSO Dimethylsulphoxide
EDC 1-Ethyl-3-(3-dimethylaminopropyl)carbodiimide
ES Electrospray
EtOAc Ethyl acetate h Hour(s)
HATU 1-[Bis(dimethylamino)methylene]-1H-1,2,3-triazolo[4,5-b]pyridinium 3-oxid hexafluorophosphate
LCMS Liquid Chromatography-Mass Spectrometry
m Multiplet (NMR signal)
MeOH Methanol
min Minute(s)
NMR Nuclear Magnetic Resonance
rt Room temperature
s Singlet (NMR signal)
SFC Supercritical fluid chromatography
TBD 1,5,7-Triazabicyclo[4.4.0]dec-5-ene
TFA Trifluoroacetic acid
THF Tetrahydrofuran Analytical Methods
LCMS Methods:

| Method B | | |
|---|---|---|
| Column | X-bridge C18, 50 × 4.6 mm, 3.5 μm or equivalent | |
| Mobile Phase | 0.1% Ammonia in Water 0.1% Ammonia in Acetonitrile | |
| Flow Rate | 1.0 mL/min | |
| Gradient | Time | % B |
| | 0.01 | 5 |
| | 5.00 | 90 |
| | 5.80 | 95 |
| | 7.20 | 95 |
| | 7.21 | 5 |
| | 10.00 | 5 |

| Method C | | |
|---|---|---|
| Column | BEH C18, 50 × 2.1 mm, 1.7 μm or equivalent | |
| Mobile Phase | 5 mM Ammonium Acetate + 0.1% Formic Acid in Water 0.1% Formic Acid in Acetonitrile | |
| Flow Rate | 0.55 mL/min | |
| Gradient | Time | % B |
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method H | | |
|---|---|---|
| Column | X-bridge C18, 50 × 4.6 mm, 3.5 μm or equivalent | |
| Mobile Phase | (A) 0.1% Ammonia in Water (B) 0.1% Ammonia in Acetonitrile | |
| Flow Rate | 1.0 mL/min | |
| Gradient | Time | % B |
| | 0.01 | 5 |
| | 5.00 | 90 |
| | 5.80 | 95 |
| | 7.20 | 95 |
| | 7.21 | 5 |
| | 10.00 | 5 |

| Method J | | |
|---|---|---|
| Column | BEH C18, 50 * 2.1 mm, 1.7 μm or equivalent | |
| Mobile Phase | (A) 5 mM Ammonium Acetate + 0.1% Formic Acid in Water (B) 0.1% Formic Acid in Acetonitrile | |
| Flow Rate | 0.45 mL/min | |
| Gradient | Time | % B |
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method M | | |
|---|---|---|
| Column | BEH C18, 50 * 2.1 mm, 1.7 μm or equivalent | |
| Mobile Phase | (A) 5 mM Ammonium Acetate + 0.1% Formic Acid in Water (B) 0.1% Formic Acid in Acetonitrile | |
| Flow Rate | 0.40 mL/min | |
| Gradient | Time | % B |
| | 0.01 | 10 |
| | 5.00 | 90 |
| | 7.00 | 100 |
| | 11.00 | 100 |
| | 11.01 | 10 |
| | 12.00 | 10 |

Long Run LCMS Methods:

| Method D-FA | | |
|---|---|---|
| Mobile phase | A | 0.1% formic acid in water |
| | B | 0.1% formic acid in acetonitrile |
| Instrument | | Agilent 1290 Infinity RRLC attached with Agilent 6120 Mass detector and Diode array Detector |
| Column | | SUNFIRE C18, 5 μ, 4.6 * 250 mm, Waters |
| Flow rate | | 1.0 mL/min |
| Column oven temperature | | Ambient |
| Run time | | 30.0 min |
| Flow rate | 1.0 mL/min | |
| Gradient: | Time | % B |
| | 0.0 | 0 |
| | 15.0 | 20 |
| | 25.0 | 100 |
| | 27.0 | 100 |
| | 27.01 | 0 |
| | 30.0 | 0 |

| Method D-NH$_3$ | | |
|---|---|---|
| Mobile phase | A | 0.1% Ammonia in water |
| | B | 0.1% Ammonia in Acetonitrile |
| Instrument | | Agilent 1290 Infinity RRLC attached with Agilent 6120 Mass detector and Diode array Detector |
| Column | | Waters, X Bridge, C18, 250 * 4.6 mm |
| Flow rate | | 1.0 mL/min |

| Method D-NH₃ | |
|---|---|
| Column oven temperature | Ambient |
| Run time | 40.0 min |

| Gradient: | Time | % B |
|---|---|---|
| | 0.00 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 0 |

| Method D-AA | | |
|---|---|---|
| Mobile phase | A | 10 mM ammonium acetate in water |
| | B | 100% Acetonitrile |

| Method D-AA | | |
|---|---|---|
| Instrument | | Agilent 1290 Infinity RRLC attached with Agilent 6120 Mass detector and Diode array Detector |
| Column | | YMC EXRS 250 C18, 4.6 * 250 mm |
| Flow rate | | 1.0 mL/min |
| Column oven temperature | | Ambient |
| Run time | | 30.0 min |

| Gradient: | Time | % B |
|---|---|---|
| | 0.0 | 5 |
| | 15.0 | 50 |
| | 20.0 | 50 |
| | 25.0 | 100 |
| | 27.0 | 100 |
| | 27.01 | 5 |
| | 30.0 | 5 |

EXAMPLE 1

(R)-1-(3-cyanophenyl)-N((1-cyanopyrrolidin-3-yl)methyl)-1H-1,2,4-triazole-3-carboxamide

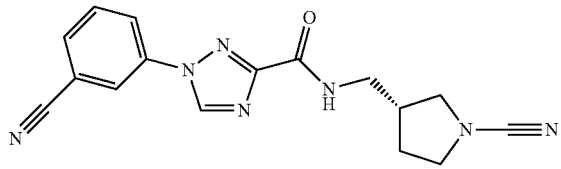

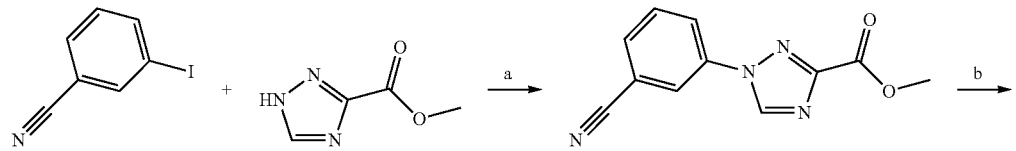

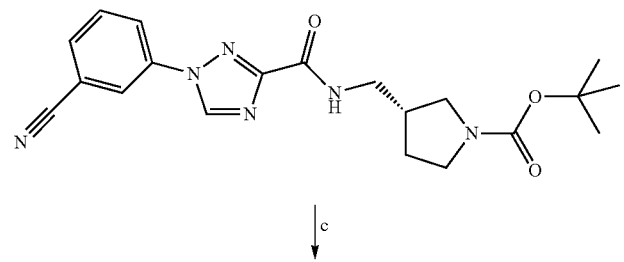

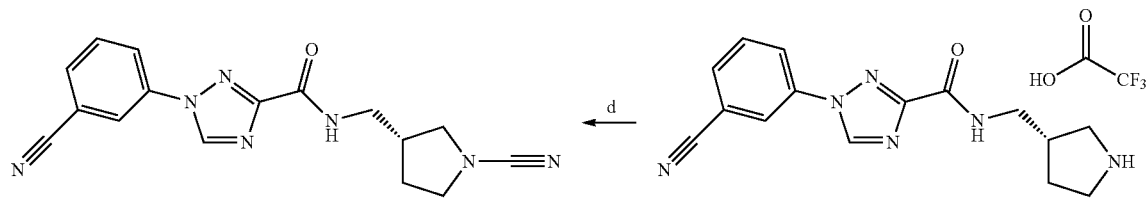

Step a.

To a stirred solution of 3-iodobenzonitrile (0.500 g, 2.18 mmol) and methyl 1H-1,2,4-triazole-3-carboxylate (CAS Number 4928-88-5; 0.277 g, 2.18 mmol) in DMSO (6 mL) was added L-proline (0.050 g, 0.44 mmol), Cu(I)I (0.083 g, 0.44 mmol) and $K_2CO_3$ (0.602 g, 4.34 mmol) at rt. The solution was heated at 80° C. for 18 h. The reaction mixture was cooled to rt and poured into ice cold water (100 mL) and extracted with EtOAc (4×50 mL). Combined organic extracts were dried over anhydrous sodium sulfate, filtered and concentrated under reduced pressure. The residue was purified by flash column chromatography (compound eluted in 35% EtOAc in hexane) yielding methyl 1-(3-cyanophenyl)-1H-1,2,4-triazole-3-carboxylate (0.105 g, 0.46 mmol). LCMS: Method H, 1.517 min, MS: ES+ 229.19.

Step b.

To a stirred solution of methyl 1-(3-cyanophenyl)-1H-1,2,4-triazole-3-carboxylate (0.100 g, 0.44 mmol) and tert-butyl (R)-3-(aminomethyl)pyrrolidine-1-carboxylate (CAS Number 199174-29-3; 0.106 g, 0.53 mmol) in THF (4 mL) was added a solution of 1,5,7-triazabicyclo[4.4.0]dec-5-ene (CAS Number 5807-14-7; 0.092 g, 0.66 mmol) in THF (1 mL) at 0° C. The resulting mixture was stirred at rt for 18h. The reaction mixture was poured into water (50 mL) and extracted with EtOAc (2×50 mL). Combined organic layers were dried over anhydrous sodium sulfate, filtered and concentrated under reduced pressure. The residue was purified by flash column chromatography (compound eluted in 5% MeOH in DCM) yielding tert-butyl (R)-3-((1-(3-cyanophenyl)-1H-1,2,4-triazole-3-carboxamido)methyl)-pyrrolidine-1-carboxylate. (0.083 g, 0.21 mmol), LCMS: Method H, 1.789 min, MS: ES+ [M−100] 297.26.

added TFA (0.37 mL) at 0° C. and stirred for 1.5 h. Volatiles were distilled off under reduced pressure and the residue azeotropically distilled with DCM (3×50 mL) and dried under high vacuum yielding (S)-1-(3-cyanophenyl)-N-(pyrrolidin-3-ylmethyl)-1H-1,2,4-triazole-3-carboxamide TFA salt, 0.110 g, crude. LCMS: Method H, 1.331 min, MS: ES+ 297.26.

Step d.

To a stirred solution of (S)-1-(3-cyanophenyl)-N-(pyrrolidin-3-ylmethyl)-1H-1,2,4-triazole-3-carboxamide TFA salt (0.100 g, crude from previous step) in THF (5 mL) was added $K_2CO_3$ (0.100 g, 0.73 mmol) at 0° C. After stirring at 0° C. for 15 min, cyanogen bromide (0.026 g, 0.24 mmol) was added and stirring continued for a further 1 h. The resulting mixture was poured into water (50 mL) and extracted with EtOAc (2×50 mL). Combined organic extracts were dried over anhydrous sodium sulfate, filtered and concentrated under reduced pressure. The residue was purified by flash column chromatography (compound eluted in 95% EtOAc in hexane) yielding (R)-1-(3-cyanophenyl)-N-((1-cyanopyrrolidin-3-yl)methyl)-1H-1,2,4-triazole-3-carboxamide (0.030 g, 0.09 mmol). LCMS: Method J, 2.767 min, MS: ES− 320.2; $^1$H NMR (400 MHz, DMSO-$d_6$) δ ppm: 9.49 (s, 1H), 8.93-8.96 (t, J=6.0 Hz, 1H), 8.44 (s, 1H), 8.23-8.25 (m, 1H), 7.93-7.95 (d, J=7.6 Hz 1H), 7.78-7.82 (m, 1H), 3.34-3.42 (m, 3H), 3.14-3.29 (m, 4H), 1.89-1.94 (m, 1H), 1.63-1.68 (m, 1H).

EXAMPLE 2

(S)-1-(3-cyanophenyl)-N-((1-cyanopyrrolidin-3-yl)methyl)-N-methyl-1H-1,2,4-triazole-3-carboxamide

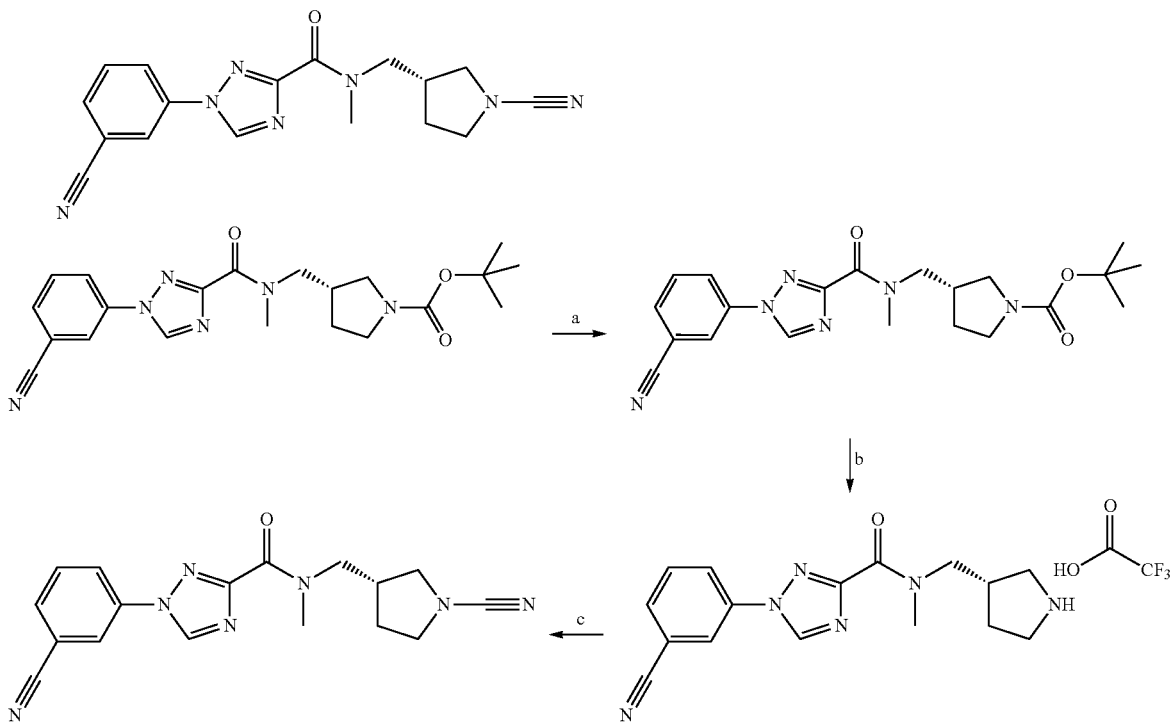

Step c.

To a stirred solution of tert-butyl (R)-3-((1-(3-cyanophenyl)-1H-1,2,4-triazole-3-carboxamido)-methyl)pyrrolidine-1-carboxylate (0.075 g, 0.189 mmol) in DCM (4 mL) was Step a.

To a stirred solution of tert-butyl (R)-3-((1-(3-cyanophenyl)-1H-1,2,4-triazole-3-carboxamido)-methyl)pyrrolidine-1-carboxylate (described in Example 1, steps a and b; 0.100 g, 0.25 mmol) in DMF (2 mL) was added NaH (60% in mineral oil; 0.008 g, 0.30 mmol) portion-wise at 0° C. After stirring for 15 min, methyl iodide (0.035 g, 0.25 mmol) was added and the resulting reaction mixture was stirred at rt for 1 h. The reaction was poured into ice water (50 mL) and extracted with EtOAc (2×50 mL). The combined organic phase was dried over anhydrous sodium sulfate, filtered and concentrated under reduced pressure. The resulting residue was purified by flash column chromatography (eluted in 2% MeOH in DCM) yielding tert-butyl (R)-3-((1-(3-cyanophenyl)-N-methyl-1H-1,2,4-triazole-3-carboxamido)methyl)-pyrrolidine-1-carboxylate (0.095 g, 0.23 mmol). LCMS: Method H, 1.755 min, MS: ES+ 411.4.

Step b.

A stirred solution of tert-butyl (R)-3-((1-(3-cyanophenyl)-N-methyl-1H-1,2,4-triazole-3-carboxamido)methyl)pyrrolidine-1-carboxylate (0.090 g, 0.22 mmol) in DCM (5 mL) was added TFA (0.45 mL) at 0° C. The reaction mixture was stirred at 0° C. to rt for 1.5h. The resulting reaction mixture was concentrated under reduced pressure. The obtained residue was azeotropically distilled with DCM (3×50 mL) and dried under high vacuum yielding (S)-1-(3-cyanophenyl)-N-methyl-N-(pyrrolidin-3-ylmethyl)-1H-1,2,4-triazole-3-carboxamide TFA salt, 0.110 g, crude. LCMS: Method H, 1.325 min, MS: ES+ 311.28.

Step c.

To a stirred solution of (S)-1-(3-cyanophenyl)-N-methyl-N-(pyrrolidin-3-ylmethyl)-1H-1,2,4-triazole-3-carboxamide TFA salt (0.100 g, crude from previous step) in THF (5 mL) was added K₂CO₃ (0.097 g, 0.71 mmol) at 0° C. After stirring for 10 min, cyanogen bromide (0.024 g, 0.24 mmol) was added and stirring continued for 1h at rt. The resulting mixture was poured into water (50 mL) and extracted with EtOAc (2×50 mL). The combined organic phase was dried over anhydrous sodium sulfate, filtered and concentrated under reduced pressure. The residue was purified by flash column chromatography (compound eluted in 2% MeOH in DCM) yielding (S)-1-(3-cyanophenyl)-N-((1-cyanopyrrolidin-3-yl)methyl)-N-methyl-1H-1,2,4-triazole-3-carboxamide (0.028 g, 0.08 mmol). LCMS: Method J, 2.723 min, MS: ES+ 336.15; $^1$H NMR (400 MHz, DMSO-d6) δ ppm: 9.48 (s, 1H), 8.42-8.43 (d, J=4.0 Hz, 1H), 8.19-8.23 (m, 1H), 7.92-7.94 (d, J=8.0 Hz, 1H), 7.77-7.81 (t, J=8 Hz 1H), 3.44-3.58 (m, 3H), 3.36-3.41 (m, 1H), 3.23-3.27 (m, 1H), 2.99-3.10 (m, 4H), 2.59-2.65 (m, 1H), 1.86-1.89 (m, 1H), 1.64-1.69 (m, 1H).

EXAMPLE 3

N((1-cyanopyrrolidin-3-yl)methyl)-1-phenyl-1H-1,2,4-triazole-3-carboxamide

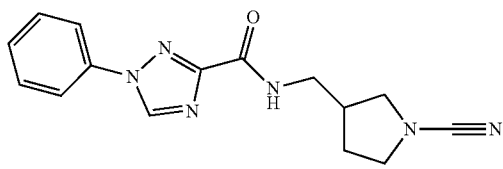 [SMILES: N#CN1CCC(CNC(=O)c2ncn(-c3ccccc3)n2)C1]

Prepared using analogous procedures to those described herein.

EXAMPLE 4

N-(((2R,3R)-1-cyano-2-methylpyrrolidin-3-yl)methyl)-1-(3-cyanophenyl)-1H-1,2,4-triazole-3-carboxamide and N-(((2R,3S)-1-cyano-2-methylpyrrolidin-3-yl)methyl)-1-(3-cyanophenyl)-1H-1,2,4-triazole-3-carboxamide

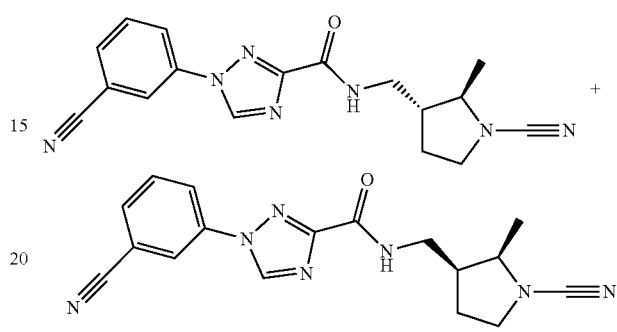

Step a.

To a solution of methyl acetoacetate (200 g, 1724.13 mmol) and 1,2-dibromoethane (179.2 mL, 2068.95 mmol) in acetone (2000 mL) was added K₂CO₃ (356.8 g, 2586.19 mmol) at rt. The reaction mixture was heated at 70° C. for 24 h. The resulting mixture was cooled to rt, filtered through celite and washed with acetone (2×100 mL). The filtrate was concentrated under reduced pressure to give a crude oil which was purified by column chromatography (4% EtOAc in hexane) to yield methyl 1-acetylcyclopropane-1-carboxylate (100 g, 704.22 mmol). LCMS: Method C, 1.47 min, MS: ES+ 143.14.

Step b.

A solution of methyl 1-acetylcyclopropane-1-carboxylate (82.0 g, 577.46 mmol) and (R)-1-phenylethan-1-amine (69.87 g, 577.46 mmol) in toluene (820 mL) was charged in a dean stark glass assembly. The reaction mixture was heated to 130° C. for 24 h (water release was collected in dean stark assembly). The reaction mixture was cooled to rt and concentrated under reduced pressure. The resulting residue was purified by column chromatography (1.5% EtOAc in hexane) to yield methyl (R)-2-methyl-1-(1-phenylethyl)-4,5-dihydro-1H-pyrrole-3-carboxylate (51.0 g, 208.16 mmol). LCMS: Method C, 1.409 min, MS: ES+ 246.40.

Step c.

To NaBH₄ (35.5 g, 936.73 mmol) was carefully added acetic acid (765 mL, 15 vol) dropwise at 0° C. and stirred for 45 min at 0° C. A solution of methyl (R)-2-methyl-1-(1-phenylethyl)-4,5-dihydro-1H-pyrrole-3-carboxylate (51.0 g, 208.16 mmol) in acetonitrile (765 mL) was then added at 0° C. and the reaction mixture was stirred for 4 h at rt. The resulting mixture was diluted with water (4000 mL) and basified with solid Na₂CO₃. The aqueous layer was extracted with EtOAc (2×3000 mL). The combined organic phase was collected, dried over Na₂SO₄, filtered and concentrated under reduced pressure. The resulting residue was dissolved in hexane and insoluble solid was removed by filtration. The filtrate was evaporated under reduced pressure to yield a mixture of diastereomers (51.0 g, 208.16 mmol). LCMS: Method D-NH₃, 28.96 min (92%, major diastereomer) and 29.114 min (7%, minor diastereomer), MS: ES+ 248.2; The diastereomeric mixture was dissolved in n-hexane (500 mL) to form a clear solution which was stirred at −78° C. for 2 h. The resulting precipitate was removed by filtration and wash with cold hexane to yield methyl (2R,3R)-2-methyl-1-((R)-1-phenylethyl)pyrrolidine-3-carboxylate (28 g, 113.36 mmol). LCMS: Method D-NH$_3$, 28.819 min, Method D-FA: 12.098 min, MS: ES+ 248.2; $^1$H NMR (400 MHz, DMSO-d$_6$) δ ppm: 7.29-7.35 (m, 4H), 7.22-7.24 (m, 1H), 3.60 (s, 3H), 3.55-3.58 (m, 1H), 3.34-3.37 (m, 1H) 3.06-3.09 (m, 1H), 2.58-2.61 (m, 1H), 2.43-2.47 (m, 1H), 1.92-1.99 (m, 1H), 1.80-1.83 (m, 1H), 1.27 (d, J=6.71 Hz, 3H), 0.71 (d, J=6.40 Hz, 3H).

Step d.

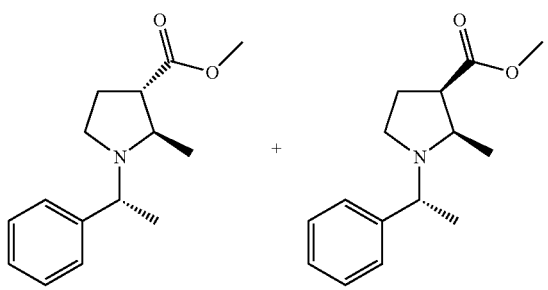 [SMILES: COC(=O)[C@H]1CCN([C@H](C)c2ccccc2)[C@@H]1C ; COC(=O)[C@@H]1CCN([C@H](C)c2ccccc2)[C@@H]1C]

Methyl (2R,3R)-2-methyl-1-((R)-1-phenylethyl)pyrrolidine-3-carboxylate (26.0 g, 105.263 mmol) was dissolved in DBU (47.99 g, 315.723 mmol) and heated at 100° C. for 24 h in seal tube. The reaction mixture was poured into water (800 mL) and extracted ethyl acetate with (3×700 mL). The combined organic layer was washed with water (100 mL), dried over Na$_2$SO$_4$ and evaporated under reduced pressure to give crude product which was purified by column chromatography (eluted at 30% ethyl acetate in hexane) to yield mixture of methyl (2R,3R)-2-methyl-1-((R)-1-phenylethyl)pyrrolidine-3-carboxylate and methyl (2R, 3S)-2-methyl-1-((R)-1-phenylethyl)pyrrolidine-3-carboxylate (22 g, 89.068 mmol). LCMS: Method D-FA, 11.94 min (21.72%) & 12.68 min (77.01%), MS: ES+ 248.4; $^1$H NMR (400 MHz, CDCl$_3$) δ ppm: 7.25-7.40 (m, 5H), 3.85-3.87 (m, 1H), 3.74 (s, 3H), 3.00-3.30 (m, 1H), 2.56-2.81 (m, 3H), 1.93-2.08 (m, 2H), 1.41 (m, 3H), 1.04 (dd, J=6.4 Hz, 3H).

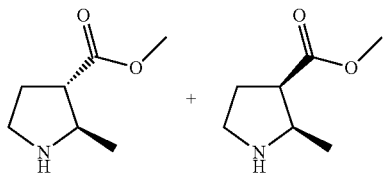

Step e.
To solution of methyl (2R,3S)-2-methyl-1-((R)-1-phenylethyl) pyrrolidine-3-carboxylate and methyl (2R,3R)-2-methyl-1-((R)-1-phenylethyl)pyrrolidine-3-carboxylate (10 g, 40.485 mmol) in methanol (100 mL) was added 1 g (10% Pd/C, 50% moisture). The reaction mixture was stirred at rt under hydrogen (40 barr) for 24 h. The resulting mixture was filtered through celit, washed with methanol (50 mL) and the filtrate was concentrated under reduced pressure to yield mixture of methyl (2R,3S)-2-methylpyrrolidine-3-carboxylate and methyl (2R,3R)-2-methylpyrrolidine-3-carboxylate (5.3 g, 37.062 mmol). LCMS: Method C, 0.31 min, MS: ES+ 144.1; $^1$H NMR (400 MHz, CDCl$_3$) δ ppm: 3.74 (s, 3H), 3.40-3.43 (m, 1H), 3.10-3.20 (m, 2H), 2.53-2.63 (m, 1H), 2.13-2.19 (m, 2H), 2.04-2.08 (m, 1H), 1.37 (dd, J=6.4 Hz, 3H).

Step f.

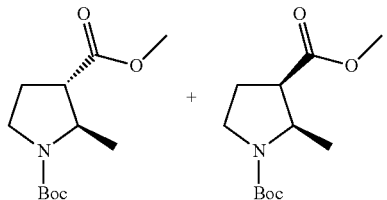 [SMILES: COC(=O)[C@H]1CCN(C(=O)OC(C)(C)C)[C@@H]1C ; COC(=O)[C@@H]1CCN(C(=O)OC(C)(C)C)[C@@H]1C]

To solution of methyl (2R,3S)-2-methylpyrrolidine-3-carboxylate and methyl (2R,3R)-2-methylpyrrolidine-3-carboxylate (5.3 g, 37.062 mmol) in THF (53 mL) were added 4-dimethylaminopyridine (0.53 g, 0.1 w/w) and di-tert-butyl dicarbonate (9.69 g, 44.449 mmol) at 0° C. under N$_2$. The reaction mixture was allowed to warm to rt and stirred for a further 16 h. The resulting mixture was diluted with water (200 mL) and extracted with ethyl acetate (3×200 mL). The combined organic layer was washed with water (200 mL), dried over Na$_2$SO$_4$ and evaporated under reduced pressure to give a crude product which was purified by column chromatography (eluted at 10% ethyl acetate in hexane) to yield mixture of 1-(tert-butyl) 3-methyl (2R, 3S)-2-methylpyrrolidine-1,3-dicarboxylate and 1-(tert-butyl) 3-methyl (2R, 3R)-2-methylpyrrolidine-1,3-dicarboxylate (8.0 g, 32.92 mmol). LCMS: Method C, 1.665 min, MS: ES+ (−56) 188; $^1$H NMR (400 MHz, CDCl$_3$) δ ppm: 4.00-4.30 (m, 1H), 3.74 (s, 3H), 3.52-3.56 (m, 1H), 3.35-3.39 (m, 1H), 2.71-2.72 (m, 1H), 2.11-2.16 (m, 2H), 1.50 (s, 9H), 1.32 (dd, J=5.6 Hz, 3H).

Step g.

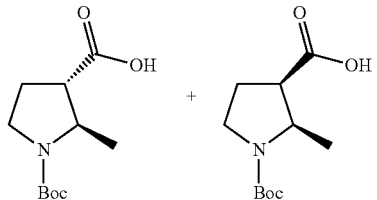 [SMILES: C[C@@H]1[C@@H](C(=O)O)CCN1C(=O)OC(C)(C)C ; C[C@@H]1[C@H](C(=O)O)CCN1C(=O)OC(C)(C)C]

To a solution of 1-(tert-butyl) 3-methyl (2R,3S)-2-methylpyrrolidine-1,3-dicarboxylate and 1-(tert-butyl)-3-methyl (2R,3R)-2-methylpyrrolidine-1,3-dicarboxylate (8.0 g, 32.921 mmol) in THF: Water (5:1) (12 mL) was added lithium hydroxide monohydrate (2.07 g, 49.381 mmol) at 0° C. The resulting reaction mixture was warmed to rt and stirred for 6 h. The mixture was poured into water (300 mL) and washed with ethyl acetate (3×300 mL). The aqueous layer was acidified with 1M HCl solution (~200 mL) and extracted with ethyl acetate (3×300 mL). The combined organic layer was dried over Na$_2$SO$_4$ and evaporated under reduced pressure to yield mixture of (2R, 3R)-1-(tert-butoxycarbonyl)-2-methylpyrrolidine-3-carboxylic acid and (2R,3S)-(tert-butoxycarbonyl)-2-methylpyrrolidine-3-carboxylic acid (6.5 g, 28.384 mmol). LCMS: Method D-AA, 8.770 min (18.63 mmol) and 9.105 min (81.37 min), MS: ES+ (−56) 156.25; $^1$H NMR (400 MHz, DMSO-d$_6$) δ ppm: 12.47 (s, 1H), 3.8-4.1 (m, 1H), 3.25-3.37 (m, 2H), 2.60-2.75 (m, 1H), 2.05-2.12 (m, 1H), 1.89-1.97 (m, 1H), 1.40 (s, 9H), 1.18 (dd, J=5.6 Hz, 3H).

Step h.

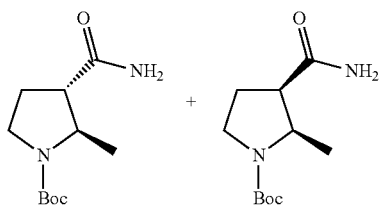 [SMILES: C[C@@H]1[C@@H](C(N)=O)CCN1C(=O)OC(C)(C)C ; C[C@@H]1[C@H](C(N)=O)CCN1C(=O)OC(C)(C)C]

To a solution of (2R, 3R)-1-(tert-butoxycarbonyl)-2-methylpyrrolidine-3-carboxylic acid and (2R,3S)-1-(tert-butoxycarbonyl)-2-methylpyrrolidine-3-carboxylic acid (5.5 g, 24.017 mmol) in THF (50 mL) were added EDC.HCl (5.50 g, 28.795 mmol) and 1-hydroxybenzotriazole hydrate (3.67 g, 23.986 mmol) at 0° C. under $N_2$. Triethylamine (16.16 mL, 120.087 mmol) and $NH_4Cl$ (6.42 g, 120.000 mmol) were added to the reaction mixture and stirred for 16 h at rt. The resulting reaction mixture was poured into saturated $NaHCO_3$ solution (400 mL) and extracted with ethyl acetate (3×400 mL). The combined organic layer was dried over $Na_2SO_4$ and evaporated under reduced pressure to give crude product which was purified by column chromatography (2% MeOH in DCM) to yield tert-butyl (2R,3R)-3-carbamoyl-2-methylpyrrolidine-1-carboxylate and tert-butyl (2R,3S)-3-carbamoyl-2-methylpyrrolidine-1-carboxylate (4.8 g, 21.056 mmol). LCMS: Method C, 1.380 min, MS: ES+ (−56) 173.2; $^1$H NMR (400 MHz, $CDCl_3$) δ ppm: 5.57 (br, 2H), 3.95-4.12 (m, 1H), 3.42-3.63 (m, 2H), 2.42-2.61 (m, 1H), 2.09-2.11 (m, 2H), 1.47 (s, 9H), 1.30 (dd, J=5.6 Hz, 3H).

Step i.

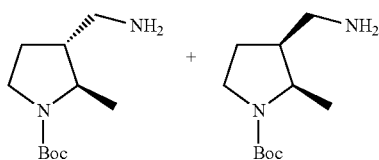

To a solution of tert-butyl (2R, 3R)-3-carbamoyl-2-methylpyrrolidine-1-carboxylate and tert-butyl (2R,3S)-3-carbamoyl-2-methylpyrrolidine-1-carboxylate (4.8 g, 21.052 mmol) in THF (20 mL) was added $BH_3$.DMS (2M in THF) (15.78 mL, 31.57 mmol) drop wise at 0° C. under $N_2$. The reaction mixture was allowed to warm to rt and stirred for 16 h at 70° C. The mixture was then cooled to rt and methanol (50 mL) added. The mixture was further heated at 80° C. for 2 h then cooled to rt, acidified with 1N HCl solution (240 mL) and extracted with ethyl acetate (3×400 mL). The aqueous layer was basified with sodium bicarbonate solution (50 mL) and extracted with ethyl acetate (3×300 mL) concentrated under reduced pressure to yield tert-butyl (2R, 3R)-3-(amino methyl)-2-methylpyrrolidine-1-carboxylate and tert-butyl (2R,3S)-3-(amino methyl)-2-methylpyrrolidine-1-carboxylate (0.137 g, 0.640 mmol). LCMS: Method C, 1.322 min, MS: ES-56+ 159.31; $^1$H NMR (400 MHz, DMSO-$d_6$) δ ppm: 3.28-3.48 (m, 3H), 3.15-3.26 (m, 1H), 2.41-2.44 (m, 1H), 1.65-2.05 (m, 2H), 1.41-1.60 (m, 3H), 1.34 (s, 9H), 0.95 (dd, J=6.4 Hz, 3H).

Step j.

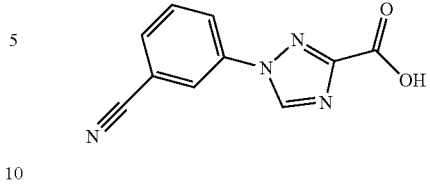

A stirred solution of methyl 1H-1,2,4-triazole-3-carboxylate (1.66 g, 13.1004 mmol) and 3-iodobenzonitrile (2 g, 8.733 mmol) in DMSO (10 mL) was added $K_2CO_3$ (3.6 g, 26.200 mmol) at rt. The reaction mixture was purged with $N_2$ for 15 min. L-proline (0.2 g, 1.746 mmol) and CuI (0.33 g, 1.746 mmol) were added at rt and the mixture was heated to 85° C. for 16 h. The mixture was then poured into water (200 mL) and extracted ethyl acetate (2×100 mL). The aqueous layer was acidified with 1M HCl solution (150 mL) and extracted with ethyl acetate (4×100 mL). The combined organic layer was washed with water (100 mL), dried over $Na_2SO_4$ and evaporated under reduced pressure to yield 1-(3-cyanophenyl)-1H-1,2,4-triazole-3-carboxylic acid (0.522 g, 63.11 mmol). LCMS: Method C, 1.29 min, MS: ES+ 215.23; $^1$H NMR (400 MHz, DMSO-$d_6$) δ ppm: 12.8 (br, 1H), 7.35 (t, J=8 Hz, 1H), 7.02 (d, J=7.6 Hz, 1H), 6.83 (s, 1H), 6.77-6.80 (dd, J=8.4 Hz, 2H).

Step k.

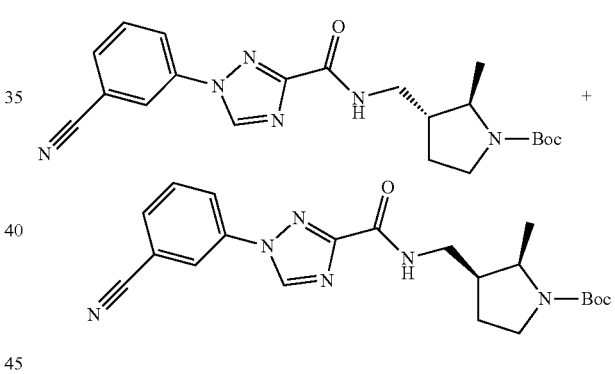

To a solution of 1-(3-cyanophenyl)-1H-1, 2, 4-triazole-3-carboxylic acid (0.156. g, 0.728 mmol) in THF (7 mL) were added HATU (0.319 g, 0.841 mmol) and DIPEA (0.232 g, 1.682 mmol) 0° C. under $N_2$. The reaction mixture was stirred for 30 min and added tert-butyl (2R, 3R)-3-(amino methyl)-2-methylpyrrolidine-1-carboxylate and tert-butyl (2R, 3S)-3-(amino methyl)-2-methylpyrrolidine-1-carboxylate (0.120 g, 0.560 mmol). The reaction mixture was become clear yellow solution and stirred at rt for 16 h. To resulting reaction mixture was added water (100 mL) and extracted with ethyl acetate (3×25 mL). The combined organic layer was washed with saturated $NaHCO_3$ solution (100 mL), dried over $Na_2SO_4$ and evaporated under reduced pressure to give crude product which was purified by Combi-flash chromatography (eluted at 0.2% MeOH in DCM) to yield tert-butyl (2R, 3R)-3-((1-(3-cyanophenyl)-1H-1, 2, 4-triazole-3-carboxamido) methyl)-2-methylpyrrolidine-1-carboxylate and tert-butyl (2R, 3S)-3-((1-(3-cyanophenyl)-1H-1, 2, 4-triazole-3-carboxamido) methyl)-2-methylpyrrolidine-1-carboxylate (0.106 g, 0.258 mmol). LCMS: Method C, 1.627 min, MS: ES+ (−100) 311.48.

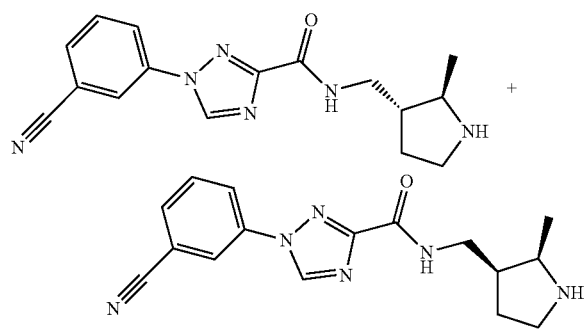

Step l.

To a solution of tert-butyl (2R, 3S)-3-((1-(3-cyanophenyl)-1H-1, 2, 4-triazole-3-carboxamido) methyl)-2-methylpyrrolidine-1-carboxylate and tert-butyl (2R, 3R)-3-((1-(3-cyanophenyl)-1H-1, 2, 4-triazole-3-carboxamido) methyl)-2-methylpyrrolidine-1-carboxylate (0.103 g, 0.251 mmol) in DCM (5 mL) was added TFA (0.2 mL, 2.512 mmol) 0° C. under $N_2$ atmosphere. The reaction mixture was allowed to warm to rt and stirred for 2 h then concentrated under reduced pressure to yield 1-(3-cyanophenyl)-N-(((2R, 3R)-2-methylpyrrolidin-3-yl) methyl)-1H-1, 2, 4-triazole-3-carboxamide trifluoroacetate and 1-(3-cyanophenyl)-N-(((2R, 3S)-2-methylpyrrolidin-3-yl) methyl)-1H-1, 2, 4-triazole-3-carboxamide trifluoroacetate (0.140 g, 0.267 mmol). LCMS: Method C, 1.286 min, MS: ES+ 311.5.

Step m.

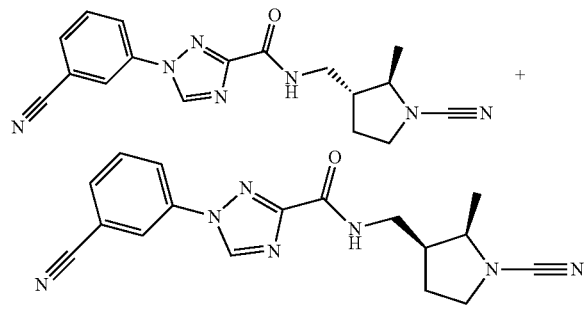

To a solution of 1-(3-cyanophenyl)-N-(((2R, 3S)-2-methylpyrrolidin-3-yl) methyl)-1H-1, 2, 4-triazole-3-carboxamide trifluoroacetate and 1-(3-cyanophenyl)-N-(((2R, 3R)-2-methylpyrrolidin-3-yl) methyl)-1H-1, 2, 4-triazole-3-carboxamide trifluoroacetate (0.139 g, 0.327 mmol) in THF (5 mL) was added $K_2CO_3$ (0.090 g, 0.654 mmol) and the mixture was stirred for 10 min. CNBr (0.034 g, 0.392 mmol) was added at rt and reaction mixture was stirred at rt for 30 min. To resulting reaction mixture was added water (50 mL) and the mixture extracted with ethyl acetate (3×50 mL). The combined organic layer was washed with water (50 mL), dried over $Na_2SO_4$ and evaporated under reduced pressure to give crude product. The crude product was purified by Combi-flash chromatography (eluted at 0.4% MeOH in DCM) to yield N-(((2R, 3R)-1-cyano-2-methylpyrrolidin-3-yl) methyl)-1-(3-cyanophenyl)-1H-1, 2, 4-triazole-3-carboxamide (0.052 g, 0.155 mmol) which was further purified by prep TLC (3% MeOH in DCM) and then prep HPLC (MeOH: ACN using 0.1% ammonia) then triturated with n-pentene (2×3 mL) to yield N-(((2R,3S)-1-cyano-2-methylpyrrolidin-3-yl)methyl)-1-(3-cyanophenyl)-1H-1,2,4-triazole-3-carboxamide and N-(((2R,3R)-1-cyano-2-methylpyrrolidin-3-yl)methyl)-1-(3-cyanophenyl)-1H-1,2,4-triazole-3-carboxamide (0.0028 g, 0.0083 mmol); LCMS: Method M, 17.82 (25.34%), 18.29 min (68.88%), MS: ES+ 336; MS: ES+336.2.

The diastereoisomers may be separable by standard methods.

EXAMPLE 5

(R)-1-(3-cyanophenyl)-N((1-cyanopyrrolidin-3-yl) methyl)-1H-1,2,3-triazole-4-carboxamide

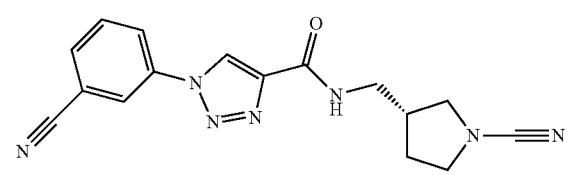 [SMILES: N#Cc1cccc(-n2cc(C(=O)NC[C@H]3CCN(C#N)C3)nn2)c1]

Step a.

To a stirred solution of sodium azide (0.424 g, 6.535 mmol) and $CuSO_4$ (0.086 g, 0.544 mmol) in MeOH (8 mL) was added (3-cyanophenyl)boronic acid (0.8 g, 5.445 mmol) (CAS number 150255-96-2, available from Combi-Blocks) at rt. The reaction mixture was stirred at rt for 16 h. Ethyl propionate (0.587 g, 5.99 mmol) and a solution of sodium L-(+)-ascorbate (0.539 g, 0.272 mmol) in water (2 mL) was added to the reaction mixture which was stirred for a further 1 h at rt. The resulting reaction mixture was filtered, washed with water (3×5 mL) and the solid was dried under reduced pressure to yield ethyl 1-(3-cyanophenyl)-1H-1,2,3-triazole-4-carboxylate (0.25 g, 1.033 mmol). LCMS: Method C, 1.579 min; MS: ES+ 243.4.

Step b. To a stirred solution of ethyl 1-(3-cyanophenyl)-1H-1,2,3-triazole-4-carboxylate (0.2 g, 0.826 mmol) and tert-butyl (R)-3-(aminomethyl)pyrrolidine-1-carboxylate (0.165 g, 0.826 mmol) (CAS number 199174-29-3, available from Synthonix) in THF (5 mL) was added a solution of TBD (0.23 g, 1.653 mmol) in THF (1 mL) dropwise at 0° C. The reaction mixture was heated at 80° C. for 16 h. The resulting reaction mixture was diluted with water (40 mL) and extracted with EtOAc (3×40 mL). The combined organic phase was dried over $Na_2SO_4$, filtered and concentrated under reduced pressure. Crude material was purified by flash column chromatography (69% EtOAc in hexane) to yield tert-butyl (R)-3-((1-(3-cyanophenyl)-1H-1,2,3-triazole-4-carboxamido)-methyl)-pyrrolidine-1-carboxylate (0.13 g, 0.328 mmol). LCMS: Method C, 1.659 min; MS: ES+ 397.48.

Step c.

To a stirred solution of tert-butyl (R)-3-((1-(3-cyanophenyl)-1H-1,2,3-triazole-4-carboxamido)-methyl)-pyrrolidine-1-carboxylate (0.12 g, 0.303 mmol) in DCM (3 mL) was added TFA (1.2 mL, 10 volumes) dropwise at 0° C. and stirred at rt for 2 h. The resulting reaction mixture was concentrated under reduced pressure and the residue was further concentrated from DCM (3×5 mL) to yield (S)-1-(3-cyanophenyl)-N-(pyrrolidin-3-ylmethyl)-1H-1,2,3-triazole-4-carboxamide trifluoroacetate (0.14 g, 0.341 mmol). LCMS: Method C, 1.249 min; MS: ES+297.43.

Step d.

To a stirred solution of (S)-1-(3-cyanophenyl)-N-(pyrrolidin-3-ylmethyl)-1H-1,2,3-triazole-4-carboxamide trifluoroacetate (0.13 g, 0.317 mmol) in THF (4 mL) was added K$_2$CO$_3$ (0.131 g, 0.951 mmol) at 0° C. and was stirred for 10 min. Cyanogen bromide (0.04 g, 0.380 mmol) was added portionwise at 0° C. and stirred at rt for 1.5 h. The resulting reaction mixture was diluted with water (30 mL) extracted with EtOAc (3×30 mL). The combined organic phase was dried over Na$_2$SO$_4$, filtered and concentrated under reduced pressure. Crude material was purified by flash column chromatography (72% EtOAc in hexane) to yield (R)-1-(3-cyanophenyl)-N-((1-cyanopyrrolidin-3-yl) methyl)-1H-1,2, 3-triazole-4-carboxamide (0.12 g, 0.374 mmol). LCMS: Method H, 2.97 min, MS: ES– 320.2; $^1$H NMR (400 MHz, CDCl$_3$) δ ppm: 8.61 (s, 1H), 8.18 (s, 1H), 8.05 (m, 1H), 7.86-7.75 (m, 2H), 7.41-7.36 (m, 1H), 3.65-3.47 (m, 4H), 3.31-3.27 (m, 1H), 2.71-2.64 (m, 1H), 2.22-2.12 (m, 1H), 1.87-1.78 (m, 1H). Chiral HPLC: 100% purity, retention time: 5.67 min CHIRAL SFC Analytical Method for title compound:

Chiral compound was analysed on Waters SFC Investigator and PDA (Photodiode array) detector. The column was used Chiralcel OX—H 250*4.6 mm, 5 micron, column flow was 4.0 mL/min and ABPR (automated back-pressure regulator) was set to 100 bar. Mobile phase were used (A) liquid carbon dioxide (Liq. CO2) and (B) 0.1% diethylamine in propan-2-ol:acetonitrile (50:50).

The UV spectra were recorded at 246 nm Lambda max. Gradient ratio was, as described below.

| % B Start | % B | Time duration |
|---|---|---|
| 5 | 50 | 5 |
| 50 | 50 | 5 |

EXAMPLE 6

(R)-1-(3-chlorophenyl)-N((1-cyanopyrrolidin-3-yl) methyl)-1H-1,2, 3-triazole-4-carboxamide

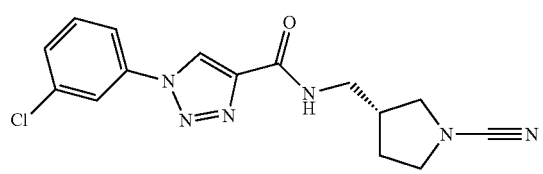 [SMILES: N#CN1CC[C@H](CNC(=O)c2cn(-c3cccc(Cl)c3)nn2)C1]

Step a.

To a stirred solution of 1-(3-chlorophenyl)-1H-1,2,3-triazole-4-carboxylic acid (0.15 g, 0.671 mmol) (CAS Number 944901-58-0, available from Synthonix) and tert-butyl (R)-3-(aminomethyl)pyrrolidine-1-carboxylate (0.134 g, 0.671 mmol) (CAS number 199174-29-3, available from Astatech) in pyridine (5 mL) was added POCl$_3$ (0.307 g, 0.19 mL, 2.013 mmol) dropwise at 0° C. and stirred at 0° C. for 40 min. The resulting reaction mixture was poured into cold water (30 mL) and extracted with EtOAc (3×30 mL). The combined organic phase was dried over Na$_2$SO$_4$, filtered and concentrated under reduced pressure. The residue was purified by flash column chromatography (70% EtOAc in hexane) to yield tert-butyl-(R)-3-((1-(3-chlorophenyl)-1H-1,2,3-triazole-4-carboxamido)-methyl)-pyrrolidine-1-carboxylate (0.235 g, 0.580 mmol). LCMS: Method C, 1.734 min; MS: ES+ 406.49.

Step b.

To a stirred solution of tert-butyl (R)-3-((1-(3-chlorophenyl)-1H-1,2,3-triazole-4-carboxamido)-methyl)-pyrrolidine-1-carboxylate (0.23 g, 0.568 mmol) in DCM (5 mL) was added TFA (2.3 mL, 10 volumes) dropwise at 0° C. and stirred at rt for 1.5 h. The resulting reaction mixture was concentrated under reduced pressure and crude was further concentrated from DCM (3×5 mL) to yield (S)-1-(3-chlorophenyl)-N-(pyrrolidin-3-ylmethyl)-1H-1,2,3-triazole-4-carboxamide trifluoroacetate (0.35 g, 0.835 mmol). LCMS: Method C, 1.341 min, MS: ES+ 306.36.

Step c.

To a stirred solution of (S)-1-(3-chlorophenyl)-N-(pyrrolidin-3-ylmethyl)-1H-1,2,3-triazole-4-carboxamide trifluoroacetate (0.34 g, 0.811 mmol) in THF (7 mL) was added K$_2$CO$_3$ (0.335 g, 2.434 mmol) at 0° C. and stirred at 0° C. for 10 min. Cyanogen bromide (0.103 g, 0.974 mmol) was added portion wise to the reaction mixture. The reaction mixture was stirred at rt for 1.5h. The resulting reaction mixture was diluted with water (50 mL) extracted with EtOAc (3×50 mL). The combined organic phase was dried over Na$_2$SO$_4$, filtered and concentrated under reduced pressure. The residue was purified by flash column chromatography (80% EtOAc in hexane) to yield (R)-1-(3-chlorophenyl)-N-((1-cyanopyrrolidin-3-yl)-methyl)-1H-1,2,3-triazole-4-carboxamide (0.13 g, 0.394 mmol). LCMS: Method H, 3.59 min; MS: ES+ 331.10; $^1$H NMR (400 MHz, DMSO-d$_6$) δ ppm: 9.38 (s, 1H), 8.97-8.94 (m, 1H), 8.14 (s, 1H), 8.01-7.99 (d, J=8.0 Hz, 1H), 7.69-7.61 (m, 2H), 3.48-3.19 (m, 7H), 2.00-1.92 (m, 1H), 1.75-1.66 (m, 1H). Chiral HPLC (method as previously shown): 100% purity, retention time: 4.42 min

EXAMPLE 7

(R)-2-(3-chlorophenyl)-N-((1-cyanopyrrolidin-3-yl) methyl)-2H-1,2,3-triazole-4-carboxamide

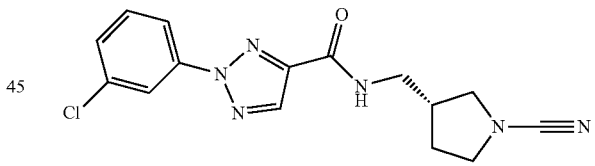

Step a.

To a stirred solution of 2-(3-chlorophenyl)-2H-1,2,3-triazole-4-carboxylic acid (0.15 g, 0.671 mmol) (CAS Number 90839-69-3, available from Enamine) and tert-butyl (R)-3-(aminomethyl)pyrrolidine-1-carboxylate (0.134 g, 0.671 mmol) (CAS number 199174-29-3, available from Astatech) in pyridine (3 mL) was added POCl$_3$ (0.307 g, 0.19 mL, 2.013 mmol) dropwise at 0° C. and the mixture was stirred for 30 min. The resulting reaction mixture was poured in to water (100 mL) and extracted with EtOAc (3×50 mL). The combined organic phase was washed with water (100 mL), dried over Na$_2$SO$_4$, filtered and concentrated under reduced pressure. The crude material was purified by flash column chromatography (42% EtOAc in hexane) to yield tert-butyl (R)-3-((2-(3-chlorophenyl)-2H-1,2,3-triazole-4-carboxamido)-methyl)-pyrrolidine-1-carboxylate (0.175 g, 0.432 mmol). LCMS: Method C, 2.014 min; MS: ES+ 350.38 (M−56).

Step b.

To a stirred solution of tert-butyl (R)-3-((2-(3-chlorophenyl)-2H-1,2,3-triazole-4-carboxamido)-methyl)-pyrrolidine-1-carboxylate (0.17 g, 0.419 mmol) in DCM (10 mL) was added TFA (0.478 g, 0.3 mL, 4.197 mmol) dropwise at 0° C. The reaction mixture was stirred at rt for 2h. The resulting reaction mixture was concentrated under reduced pressure and crude was further concentrated from DCM (3×5 mL) to yield (S)-2-(3-chlorophenyl)-N-(pyrrolidin-3-ylmethyl)-2H-1,2,3-triazole-4-carboxamide trifluoroacetate (0.339 g, 0.809 mmol). LCMS: Method C, 1.374 min; MS: ES+ 306.31.

Step c.

A solution of (S)-2-(3-chlorophenyl)-N-(pyrrolidin-3-ylmethyl)-2H-1,2,3-triazole-4-carboxamide trifluoroacetate (0.335 g, 0.799 mmol) in THF (10 mL) was added $K_2CO_3$ (0.22 g, 1.599 mmol) and the mixture was stirred for 10 min at 0° C. Cyanogen bromide (0.102 g, 0.959 mmol) was added portionwise in to the reaction mixture and stirred at rt for 45 min. The resulting reaction mixture was diluted with water (50 mL) extracted with EtOAc (3×25 mL). The combined organic phase was washed with water (50 mL), dried over $Na_2SO_4$, filtered and concentrated under reduced pressure. The residue was purified by flash column chromatography (45% EtOAc in hexane) and by trituration with n-hexane (2×15 mL) to yield (R)-2-(3-chlorophenyl)-N-((1-cyanopyrrolidin-3-yl)-methyl)-2H-1,2,3-triazole-4-carboxamide (0.094 g, 0.284 mmol). LCMS: Method J, 3.99 min, MS: ES+ 331.4; $^1$H NMR (400 MHz, $CDCl_3$) δ ppm: 8.31 (s, 1H), 8.17 (s, 1H), 8.05-8.03 (m, 1H), 7.52-7.44 (m, 2H), 7.08-6.99 (m, 1H), 3.65-3.47 (m, 5H), 3.32-3.27 (m, 1H), 2.73-2.66 (m, 1H), 2.20-2.13 (m, 1H), 1.88-1.79 (m, 1H). Chiral HPLC: 100% purity, retention time: 14.05 min. Chiral compound was analysed on Agilent 1200 series HPLC and PDA detector. The column was used Chiralcel OJ-H 250*4.6 mm, 5 micron, column flow was 1.0 mL/min. Mobile phase were used (A) 0.1% diethylamine in hexane and (B) 0.1% diethylamine in propan-2-ol:methanol (50:50). The UV spectra were recorded at 272 nm Lambda max. Gradient ratio was, as described below.

| Time | % A | % B |
|---|---|---|
| 0.01 | 90 | 10 |
| 5 | 85 | 15 |
| 10 | 65 | 35 |
| 15 | 45 | 55 |
| 20 | 35 | 65 |
| 25 | 35 | 65 |
| 25.01 | 90 | 10 |
| 30 | 90 | 10 |

EXAMPLE 8

(R)—N((1-cyanopyrrolidin-3-yl)methyl)-1-phenyl-1H-1,2,4-triazole-3-carboxamide

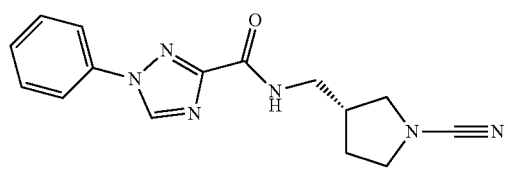 [SMILES: N#CN1CC[C@H](CNC(=O)c2ncn(-c3ccccc3)n2)C1]

May be prepared using analogous procedures to those described herein.

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue
USP30 Biochemical IC50 Assay Dilution plates were prepared at 21 times the final concentration (2100 μM for a final concentration of 100 μM) in 50% DMSO in a 96-well polypropylene V-bottom plate (Greiner #651201). A typical 8-point dilution series would be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 μl/well and 10 μl of diluted USP30 was added to the compound. Enzyme and compound were incubated for 30 min at room temp. Reactions were initiated by the addition of 50 nM of TAMRA labelled peptide linked to ubiquitin via an isopeptide bond as fluorescence polarisation substrate. Reactions were read immediately after addition of substrate and following a 2-hour incubation at room temperature. Readings were performed on a Pherastar Plus (BMG Labtech). λ Excitation 540 nm; λ Emission 590 nm.

Activity of Exemplary Compounds in USP30 biochemical IC50 assay
Ranges:
A*<0.01 μM;
0.01<A<0.1 μM;
0.1<13<1 μM;
1<C<10 μM;
D>10 μM

| Example | IC50 |
|---|---|
| 1 | A* |
| 2 | A |
| 3 | B |
| 4 | A |
| 5 | B |
| 6 | B |
| 7 | A* |

The invention claimed is:

1. A compound of formula (I), which is selected from (Ia), (Ib), and (Ic):

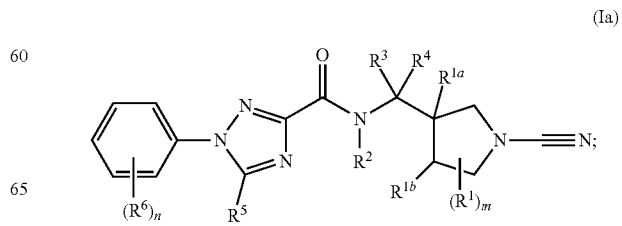

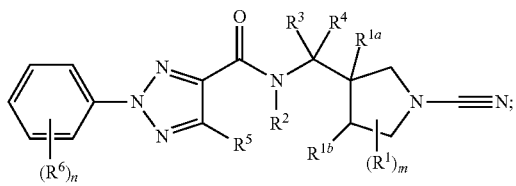

(Ib)

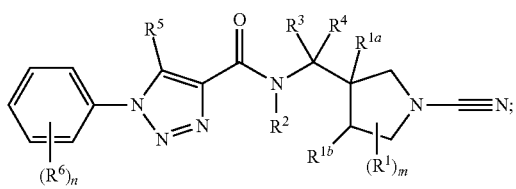

(Ic)

or a tautomer thereof, or a pharmaceutically acceptable salt of said compound or tautomer,
wherein:
m is 0 to 5;
n is 0 to 5;
each R is independently selected from halo, cyano, hydroxy, $(C_1\text{-}C_6)$alkyl, $(C_1\text{-}C_6)$alkoxy, halo$(C_1\text{-}C_6)$alkyl, halo$(C_1\text{-}C_6)$alkoxy, and $(C_1\text{-}C_6)$alkoxy$(C_1\text{-}C_6)$alkyl;
$R^{1a}$ and $R^{1b}$, are each independently selected from hydrogen, halo, cyano, hydroxy, $(C_1\text{-}C_6)$alkyl, $(C_1\text{-}C_6)$alkoxy, halo$(C_1\text{-}C_6)$alkyl, halo$(C_1\text{-}C_6)$alkoxy, and $(C_1\text{-}C_6)$alkoxy$(C_1\text{-}C_6)$alkyl;
$R^2$ is selected from hydrogen, $(C_1\text{-}C_6)$alkyl, and $(C_1\text{-}C_6)$alkoxy$(C_1\text{-}C_6)$alkyl;
or $R^{1b}$ together with $R^2$ form a 5 to 6-membered heterocyclic ring containing 1 to 2 heteroatoms independently selected from N, O and S, at least one of which is N;
said heterocyclic ring may be optionally further substituted with 1 to 4 substituents independently selected from halo, cyano, hydroxy, oxo, $(C_1\text{-}C_6)$alkyl, $(C_1\text{-}C_6)$alkoxy, $(C_1\text{-}C_6)$alkoxy$(C_1\text{-}C_6)$alkyl, halo$(C_1\text{-}C_6)$alkyl, and halo$(C_1\text{-}C_6)$alkoxy;
$R^3$ and $R^4$ are each independently selected from hydrogen, cyano, and $(C_1\text{-}C_6)$alkyl; or $R^3$ and $R^4$ together form a 3 to 6 membered cycloalkyl ring;
$R^5$ is selected from hydrogen, halo, cyano, hydroxy, $(C_1\text{-}C_6)$alkyl, $(C_1\text{-}C_6)$alkoxy, $(C_1\text{-}C_6)$alkoxy$(C_1\text{-}C_6)$alkyl, halo$(C_1\text{-}C_6)$alkyl, halo$(C_1\text{-}C_6)$alkoxy, NH$(C_1\text{-}C_6)$alkyl, N$((C_1\text{-}C_6)$alkyl$)_2$, C(O)NH$(C_1\text{-}C_6)$alkyl, C(O)N$((C_1\text{-}C_6)$alkyl$)_2$, NHC(O)$(C_1\text{-}C_6)$alkyl, N$((C_1\text{-}C_6)$alkyl)C(O)$(C_1\text{-}C_6)$alkyl), C(O)$(C_1\text{-}C_6)$alkyl, C(O)O$(C_1\text{-}C_6)$alkyl, CO$_2$H, CONH$_2$, SO$_2$NH$(C_1\text{-}C_6)$alkyl, and SO$_2$N$((C_1\text{-}C_6)$alkyl$)_2$; and
each $R^6$ is independently selected from halo, cyano, hydroxy, $(C_1\text{-}C_6)$alkyl, $(C_1\text{-}C_6)$alkoxy, $(C_1\text{-}C_6)$alkoxy$(C_1\text{-}C_6)$alkyl, halo$(C_1\text{-}C_6)$alkyl, halo$(C_1\text{-}C_6)$alkoxy, NH$(C_1\text{-}C_6)$alkyl, N$((C_1\text{-}C_6)$alkyl$)_2$, C(O)NH$(C_1\text{-}C_6)$alkyl, C(O)N$((C_1\text{-}C_6)$alkyl$)_2$, NHC(O)$(C_1\text{-}C_6)$alkyl, N$((C_1\text{-}C_6)$alkyl)C(O)$(C_1\text{-}C_6)$alkyl), C(O)$(C_1\text{-}C_6)$alkyl, C(O)O$(C_1\text{-}C_6)$alkyl, CO$_2$H, CONH$_2$, SO$_2$NH$(C_1\text{-}C_6)$alkyl, and SO$_2$N$((C_1\text{-}C_6)$alkyl$)_2$.

2. The compound according claim 1, wherein m is 0, 1 or 2.

3. The compound according to claim 2, wherein $R^1$ is selected from chloro, fluoro, methyl, ethyl, and methoxy.

4. The compound according to claim 1, wherein $R^{1a}$ is selected from hydrogen, chloro, fluoro, cyano, hydroxy, methyl, ethyl, methoxy, and methoxymethyl.

5. The compound according to claim 1, wherein $R^{1b}$ is selected from hydrogen, chloro, fluoro, cyano, hydroxy, methyl, ethyl, methoxy, and methoxymethyl.

6. The compound according to claim 1, wherein $R^2$ is selected from hydrogen and methyl.

7. The compound according to claim 1, wherein $R^{1b}$ together with $R^2$ forms a 5 to 6-membered heterocyclic ring containing 1 to 2 heteroatoms independently selected from N, O and S, at least one of which is N;
wherein said heterocyclic ring may be optionally further substituted with 1 to 2 substituents independently selected from fluoro, chloro, cyano, hydroxy, oxo, methyl, and methoxy.

8. The compound according to claim 1, wherein $R^3$ is selected from hydrogen and methyl.

9. The compound according to claim 1, wherein $R^4$ is selected from hydrogen, cyano and methyl.

10. The compound according to claim 1, wherein $R^5$ is selected from hydrogen, chloro, fluoro, cyano, hydroxy, methyl, ethyl, propyl, methoxy, ethoxy, and methoxymethyl.

11. The compound according to claim 1, wherein n is 0, 1, or 2; and each $R^6$ is independently selected from chloro, fluoro, cyano, hydroxy, methyl, ethyl, propyl, methoxy, ethoxy, methoxymethyl, CF$_3$, and OCF$_3$.

12. The compound according to claim 11, wherein each $R^6$ is independently selected from chloro and cyano.

13. The compound according to claim 1, which is selected from:
(R)-1-(3-cyanophenyl)-N-((1-cyanopyrrolidin-3-yl)methyl)-1H-1,2,4-triazole-3-carboxamide;
(S)-1-(3-cyanophenyl)-N-((1-cyanopyrrolidin-3-yl)methyl)-N-methyl-1H-1,2,4-triazole-3-carboxamide;
N-((1-cyanopyrrolidin-3-yl)methyl)-1-phenyl-1H-1,2,4-triazole-3-carboxamide;
N-(((2R)-1-cyano-2-methylpyrrolidin-3-yl)methyl)-1-(3-cyanophenyl)-1H-1,2,4-triazole-3-carboxamide;
N-(((2R,3R)-1-cyano-2-methylpyrrolidin-3-yl)methyl)-1-(3-cyanophenyl)-1H-1,2,4-triazole-3-carboxamide;
N-(((2R,3S)-1-cyano-2-methylpyrrolidin-3-yl)methyl)-1-(3-cyanophenyl)-1H-1,2,4-triazole-3-carboxamide;
(R)-1-(3-cyanophenyl)-N-((1-cyanopyrrolidin-3-yl)methyl)-1H-1,2,3-triazole-4-carboxamide;
(R)-1-(3-chlorophenyl)-N-((1-cyanopyrrolidin-3-yl)methyl)-1H-1,2,3-triazole-4-carboxamide;
(R)-2-(3-chlorophenyl)-N-((1-cyanopyrrolidin-3-yl)methyl)-2H-1,2,3-triazole-4-carboxamide; and
(R)—N-((1-cyanopyrrolidin-3-yl)methyl)-1-phenyl-1H-1,2,4-triazole-3-carboxamide;
or a tautomer thereof, or a pharmaceutically acceptable salt of said compound or tautomer.

14. A method of inhibiting USP30 in a mammal in need thereof, comprising administering to said mammal a therapeutically effective amount of a compound according to claim 1, or a tautomer thereof, or a pharmaceutically acceptable salt of said compound or tautomer.

15. A pharmaceutical composition, comprising a compound of formula (I) according to claim 1, or a pharmaceutically acceptable salt of said compound or tautomer, together with a pharmaceutically acceptable diluent or carrier.

16. A compound, which is selected from formulae (IIa), (IIIa), (IIIb), (b), (IIc), and (IIIc):

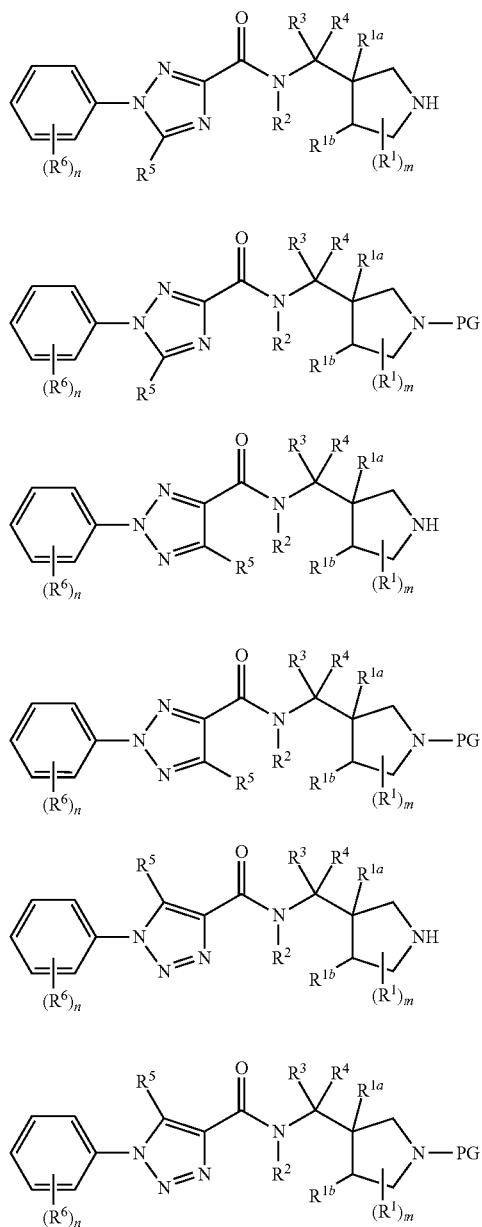

or a tautomer thereof, or a salt of said compound or tautomer, wherein:
PG is a protecting group;
m is 0 to 5;
n is 0 to 5 for formulae (IIa), (IIIa), (IIIb), (IIc) and (IIIc), and n is 1 or 2 for formula (IIb);
each $R^1$ is independently selected from halo, cyano, hydroxy, $(C_1-C_6)$alkyl, $(C_1-C_6)$alkoxy, halo$(C_1-C_6)$alkyl, halo$(C_1-C_6)$alkoxy, and $(C_1-C_6)$alkoxy$(C_1-C_6)$alkyl;
$R^{1a}$ and $R^{1b}$, are each independently selected from hydrogen, halo, cyano, hydroxy, $(C_1-C_6)$alkyl, $(C_1-C_6)$alkoxy, halo$(C_1-C_6)$alkyl, halo$(C_1-C_6)$alkoxy, and $(C_1-C_6)$alkoxy$(C_1-C_6)$alkyl;
$R^2$ is selected from hydrogen, $(C_1-C_6)$alkyl, and $(C_1-C_6)$alkoxy$(C_1-C_6)$alkyl;
or $R^{1b}$ together with $R^2$ form a 5 to 6-membered heterocyclic ring containing 1 to 2 heteroatoms independently selected from N, O and S, at least one of which is N;
said heterocylic ring may be optionally further substituted with 1 to 4 substituents independently selected from halo, cyano, hydroxy, oxo, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy;
$R^3$ and $R^4$ are each independently selected from hydrogen, cyano, and $(C_1-C_6)$alkyl; or $R^3$ and $R^4$ together form a 3 to 6 membered cycloalkyl ring;
$R^5$ for compounds of formula (IIa), (IIIa) (IIb), (IIIb) and (IIIc) is independently selected from hydrogen, halo, cyano, hydroxy, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy, $NH(C_1-C_6)$alkyl, $N((C_1-C_6)$alkyl$)_2$, $C(O)NH((C_1-C_6)$alkyl, $C(O)N((C_1-C_6)$alkyl$)_2$, $NHC(O)(C_1-C_6)$alkyl, $N((C_1-C_6)$alkyl)$C(O)(C_3-C_6)$alkyl, $C(O)(C_1-C_6)$alkyl, $C(O)O(C_1-C_6)$alkyl, $CO_2H$, $CONH_2$, $SO_2NH(C_1-C_6)$alkyl, and $SO_2N((C_1-C_6)$alkyl$)_2$;
$R^5$ for compounds of formula (IIc) is selected from hydrogen, halo, cyano, hydroxy, $(C_1-C_6)$alkyl, $(C_1-C_6)$alkoxy, $(C_1-C_6)$alkoxy$(C_1-C_6)$alkyl, halo$(C_1-C_6)$alkoxy, $NH(C_1-C_6)$alkyl, $N((C_1-C_6)$alkyl, $C(O)NH(C_1-C_6)$alkyl, $C(O)N((C_1-C_6)$alkyl$)_2$, $NHC(O)(C_1-C_6)$alkyl$_2$, $N((C_1-C_6)$alkyl)$C(O)(C_1-C_6)$alkyl), $C(O)(C_1-C_6)$alkyl, $C(O)O(C_1-C_6)$alkyl, $CO_2H$, $CONH_2$, $SO_2NH(C_1-C_6)$alkyl, and $SO_2N((C_1-C_6)$alkyl$)_2$; and
each $R^6$ is independently selected from halo, cyano, hydroxy, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy, $NH(C_1-C_6)$alkyl, $N((C_1-C_6)$alkyl$_2$, $C(O)NH(C_1-C_6)$alkyl, $C(O)N((C_1-C_6)$alkyl$)_2$, $NHC(O)(C_1-C_6)$alkyl, $N((C_1-C_6)$alkyl)$C(O)(C_1-C_6)$alkyl, $C(O)(C_1-C_6)$alkyl, $C(O)O(C_1-C_6)$alkyl, $CO_2H$, $CONH_2$, $SO_2NH((C_1-C_6)$alkyl, and $SO_2N((C_1-C_6)$alkyl$)_2$.

* * * * *

UNITED STATES PATENT AND TRADEMARK OFFICE
CERTIFICATE OF CORRECTION

Page 1 of 1

PATENT NO. : 11,059,809 B2
APPLICATION NO. : 16/615709
DATED : July 13, 2021
INVENTOR(S) : Stockley et al.

It is certified that error appears in the above-identified patent and that said Letters Patent is hereby corrected as shown below:

In the Claims

At Column 37, Line 25, "R" should be printed as "R1.".

At Column 38, Line 67, --(IIb),-- should be inserted and "(b)," removed.

At Column 40, Line 18, "heterocylic" should be printed as "heterocyclic.".

At Column 40, Line 21, --and-- should be inserted after "halo(C1 C6)alkyl,".

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*